US010456559B2

(12) United States Patent
Wilborn et al.

(10) Patent No.: US 10,456,559 B2
(45) Date of Patent: Oct. 29, 2019

(54) CANNULATED TUBE PROTECTOR, APPARATUS OPERABLE TO FACILITATE THE FLOW OF FLUIDS THROUGH A CANNULATED SITE AND APPARATUS OPERABLE TO PROTECT AND MAINTAIN POSITIONING OF A CATHETER

(71) Applicant: Marie-Andrea I Wilborn, Melbourne, FL (US)

(72) Inventors: Marie-Andrea I Wilborn, Melbourne, FL (US); Marie Therese R. Fongemie, Melbourne, FL (US)

(73) Assignee: Marie-Andrea I. Wilborn, Melbourne, FL (US)

( * ) Notice: Subject to any disclaimer, the term of this patent is extended or adjusted under 35 U.S.C. 154(b) by 0 days.

(21) Appl. No.: 16/183,789

(22) Filed: Nov. 8, 2018

(65) Prior Publication Data
US 2019/0134352 A1     May 9, 2019

Related U.S. Application Data

(63) Continuation-in-part of application No. 15/941,118, filed on Mar. 30, 2018, now Pat. No. 10,173,036, which is a continuation of application No. 14/699,766, filed on Apr. 29, 2015, now Pat. No. 9,950,143, which is a continuation-in-part of application No. 13/367,498, filed on Feb. 7, 2012, now abandoned.

(51) Int. Cl.
*A61M 25/02*    (2006.01)
*A61F 5/058*    (2006.01)
*A61F 15/00*    (2006.01)
*A61F 13/02*    (2006.01)
*A61F 13/10*    (2006.01)
*A61F 13/00*    (2006.01)

(52) U.S. Cl.
CPC ............ *A61M 25/02* (2013.01); *A61F 5/058* (2013.01); *A61F 13/0273* (2013.01); *A61F 13/101* (2013.01); *A61F 15/008* (2013.01); *A61F 2013/0028* (2013.01); *A61F 2013/00272* (2013.01); *A61F 2013/00412* (2013.01); *A61M 2025/026* (2013.01)

(58) Field of Classification Search
CPC ... A61M 25/02; A61F 15/008; A61F 13/0273; A61F 13/101; A61F 5/058
See application file for complete search history.

(56) References Cited

U.S. PATENT DOCUMENTS 5,690,610 A  *  11/1997  Ito ...................... A61F 13/0203
                                                      602/46
6,043,408 A  *   3/2000  Geng ................... A61F 13/023
                                                      602/54

* cited by examiner

*Primary Examiner* — Bradley J Osinski
(74) *Attorney, Agent, or Firm* — Mark Malek; Paul J. Ditmyer; Widerman Malek, PL

(57) ABSTRACT

A cannulated tube protector comprising a main body, a first pair of securing members extending from the main body, a second pair of securing members extending from the main body, and a splinting member comprising a viewing door. The viewing door is structured to open thereby exposing a viewing aperture, defined as a doorway. The doorway extends from a first surface of the main body to an opposing second surface of the main body.

20 Claims, 12 Drawing Sheets

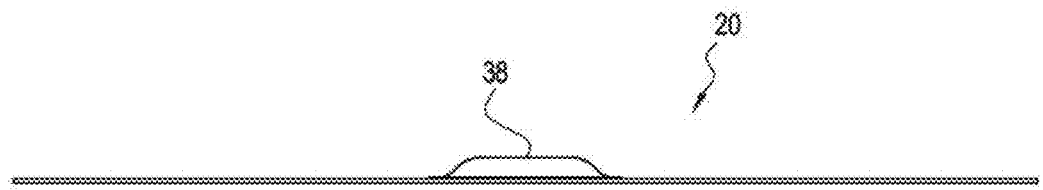
Fig. 5
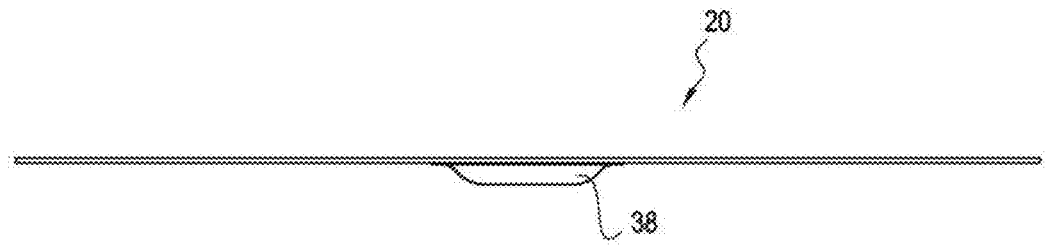
Fig. 6
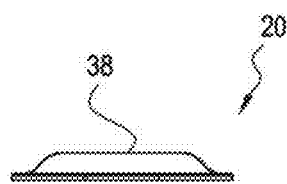 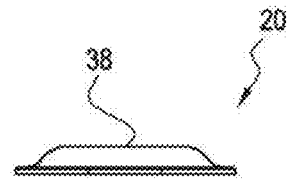
Fig. 7   Fig. 8

CANNULATED TUBE PROTECTOR, APPARATUS OPERABLE TO FACILITATE THE FLOW OF FLUIDS THROUGH A CANNULATED SITE AND APPARATUS OPERABLE TO PROTECT AND MAINTAIN POSITIONING OF A CATHETER

RELATED APPLICATIONS

This application is a continuation-in-part application and claims the benefit under 35 U.S.C. § 120 of U.S. patent application Ser. No. 15/941,118, filed on Mar. 30, 2018 titled Apparatus Operable to Protect and Maintain Positioning of an IV Catheter, which, in turn, is a continuation application of U.S. patent application Ser. No. 14/699,766, now U.S. Pat. No. 9,950,143, filed on Apr. 29, 2015, titled Intravenous Splint Cover and Associated Methods, which, in turn, is a continuation-in-part application of U.S. patent application Ser. No. 13/367,498, filed on Feb. 7, 2012, titled Intravenous Splint Cover and Associated Methods, the entire content(s) of each of which are incorporated herein by reference except to the extent that disclosure therein conflicts with disclosure herein.

FIELD OF THE INVENTION

The present invention relates to the medical field and, more specifically, to the field of intravenous splint covers and associated methods.

BACKGROUND

It can sometimes be uncomfortable when patients require medical treatment that involves an intravenous line (IV). Although IV medical treatment is very common, and is a routine way to deliver medication, the starting of an IV is generally a process that many patients do not like, i.e., being stuck with a needle. In some instances, an IV may come out, i.e., require reinsertion, thereby causing discomfort to the patient, and exposing the patient to possible infection. Another issue that may arise is occlusion of the IV due to the bending of an IV tube.

There have been attempts to prevent an IV from coming out such as, for example, immobilizing the patient's extremity where the IV is positioned. U.S. Pat. No. 4,425,913 to Lewis discloses a splint for supporting the hand, wrist and forearm of a patient when the patient is connected to an IV. The splint incorporates a substantially rigid molded body. Accordingly, use of the splint disclosed in the Lewis '913 patent immobilizing a patient's extremity and can be uncomfortable for the patient. U.S. Pat. No. 3,776,225 to Lonardo also discloses a splint for supporting and maintaining a patient's forearm immobile while receiving an IV injection. Similar to the Lewis '913 patent, the Lonardo '225 patent is directed to immobilizing the patient's extremity and suffers from the same deficiency. Further, in cases where a patient may have edema, such devices do not stretch, which may cause fluid collection and clotting, which can, in turn, be problematic.

U.S. Pat. No. 7,182,088 to Jenkins discloses yet another arm immobilizer to be used when a patient is receiving IV treatments. The immobilizer described in the Jenkins '088 patent includes a closable sleeve of a compressible material which can be placed around the patient's arm above and below the elbow joint with an opening on the inside of the arm position to give access to the IV site. Although the device described in the Jenkins '088 patent provides for smaller movements of the patient's arm, it is still designed to prevent excesses flexure movement of the elbow. Further, this device uses metal and plastic materials in its construction. Accordingly, such device can be uncomfortable for the patient to wear on receiving IV treatments. This device can also impede circulation by constriction and limited extremity movement.

U.S. Pat. No. 7,799,001 to Bierman discloses a catheter securement device that holds a medical article upon the body of the patient and inhibits longitudinal movement of the medical article as can be seen in the figure below. The device disclosed in the Bierman '001 patent includes a central channel into which a portion of the IV may be inserted. Such a device may, however, be uncomfortable for patient, and may still inhibit flexural movement of the patient's extremity. This device's only purpose is to prevent dislodging of the catheter, needle, etc. and does not prevent bending or kinking of the catheter, needle, etc. Further, the device illustrated in the Bierman '001 patent may be expensive to manufacture.

U.S. Pat. No. 3,196,870 to Sprecher et al. discloses a limb immobilizer for intravenous feeding. This immobilizer may be used to cause the limb of the patient to remain straight and immobile while receiving IV treatments. More particularly, the illustrated version of the Sprecher et al. '870 patent is directed to immobilizing the upper and lower arms of a human to prevent movement of the elbow joint, thereby facilitating intravenous administration of food, blood or other fluids. This device is made of uncomfortable materials, such as metals and plastics. Such a system depicts the very problem that needs to be addressed, i.e., immobilization of the extremities of the patient, thereby causing discomfort.

U.S. Pat. No. 7,294,752 to Propp discloses a window-dressing with an integral anchor that includes a fabric layer having an insertion site viewing member. More specifically, and as perhaps best illustrated in FIG. 4 of Propp, the dressing includes a window through which the intravenous site may be readily viewed at all times while the device is in use. The Propp dressing is positioned over an insertion point of an intravenous site so that the catheter remains visible to both the medical professional and the patient. The remainder of the catheter, needle, etc. is positioned over the splinting member of the device. Such a device allows patients to view the insertion point at all times, even when a patient would desire not to view the insertion point. This can be an issue with patients that may suffer from dementia who may attempt to rip out an IV, or young patients that may be anxious from the sight of the IV. In addition, such a device may still inhibit flexural movement of the patient's extremity. This device is a clear dressing with an anchor to prevent dislodging of the catheter, needle, etc. and does not prevent bending or kinking of the catheter, needle, etc. Further, the device may be expensive to manufacture.

U.S. Pat. No. 5,702,371 to Bierman discloses a side loaded securement device using an anchoring device to securely anchor a catheter and fluid supply to a patient's skin as illustrated in FIG. 1 thereof. Such a device may, however, be uncomfortable for the patient, and may still inhibit flexural movement of the patient's extremity. Further, the device may be expensive to manufacture and may require specific tubing, catheters, needles, etc. so that they can matingly engage the device. Another disadvantage of the Bierman device is that it still allows for a patient to readily view the IV site, which causes the same issues referenced above with respect to the Propp reference. This device is used to prevent dislodging of the catheter, needle, etc. and does not prevent bending or kinking of the catheter, needle, etc.

U.S. patent application Ser. No. 12/027,963 by Chong discloses a particular adhesive material applied to the bottom portions of the securing members having stronger adhesive properties than the adhesive material that is applied to the main body as illustrated in FIG. 9 thereof. The device in Chong, however, discloses applying a stronger adhesive to different areas of the base of a medical device, but not to the securing members when they are separate from the main body. In addition, Chong is not an intravenous splint cover and does not allow any flexural movement of a patient's extremity when a catheter, needle, etc. is in place.

U.S. Pat. No. 5,084,026 to Shapiro discloses an anchor pad with straps for securing the pad to an extremity of a patient. Two latch arrangements for holding the tubing and needle section of an intravenous apparatus are attached to the top face of the pad. Shapiro suffers from the same defects as the '371 Bierman reference. This device is an anchor and does not protect the catheter, needle, etc. or the IV site.

U.S. Pat. No. 3,490,448 to Grubb discloses a surgical bandage with an adhesive backing, a thick, sterile pressure pad, and a pair of removable protective strips as illustrated in FIGS. 9 and 10 thereof. The device is specifically used when a needle is removed from the skin of a patient. The device described in Grubb is used to apply pressure over the puncture to minimize bleeding. The device disclosed in Grubb cannot be used over an intravenous site as it will prevent the flow of fluid through the IV line and into the patient. In other words, the device described in Grubb is a pressure device that is used to prevent the flow of fluid (for example blood) at the IV site, i.e., where the puncture is made using the needle. Grubb only describes the thick, sterile pressure pad attached to the backing forming a wound contacting area. The device is a pressure bandage only used after a catheter, needle, etc. has been removed.

U.S. Pat. No. 5,891,074 to Cesarczyk discloses a device that puts pressure on the intravenous wound site, thus acting as a pressure wound dressing as illustrated in FIGS. 7 and 8 thereof. The pressure exerting support member of the device is designed with two substantially planar surfaces with the second surface extending from the first surface at an angle away from the flexible support layer at an acute angle. The pliant absorbent material layer is placed against the wound site, not over the entire intravenous site. Once the needle is removed, the device is attached firmly to the patient over the wound site. Cesarczyk suffers from the same defects as the '448 Grubb reference in that it is inappropriate for use in connection with the delivery of fluid through an IV. Instead, the device described in the Cesarczyk is adapted to be used after an IV has been removed so that the wound created by the IV on the patient's skin may be readily healed. This device, along with the device described in the Grubb reference, are inappropriate for simultaneous use with an IV and/or IV therapy.

As can be seen in FIG. 17, when an IV and IV tube are in a working position, the IV and IV tube are not bent or kinked so as to allow the ready flow of fluids.

When a patient bends his/her arm, however, or any adjacent extremity to an IV site, shifting, kinking or bending of a flexible catheter, needle, cannula, flexible tube, etc. in the vein located in a bend of the patient's extremity is not addressed by any of these devices. Compression of the catheter, needle, cannula, flexible tube, etc. against the vessel wall is also a problem with these devices. As can be seen in FIG. 18, pivoting of a joint or bony area causing bending and kinking of the catheter, needle, cannula, flexible tube, etc. or a positional IV often causes compression of a flexible catheter, needle, cannula, flexible tube, etc. against a bony prominence restricting IV therapy, i.e., transfer of a substance, such as a fluid, into a patient.

In addition, in the prior art, the IV site is either covered so that it is not accessible and/or viewable, without the ability to view or palpate, covered with a transparent material, or not addressed by the prior art device. No flexibility exists in these viewing conditions. There is no device that covers the IV site, thus preventing accidental viewing of the IV site, except when desired, such as when a medical professional needs to view the IV site. Instead, the patient can either always view the IV site or the device must be removed to allow a person to view the IV site, thus requiring another device to be used. Accordingly, a need exists for an intravenous splint cover that does not restrict movement of the patient and that allows the patient to engage in activities of daily living. There also exists a need for an intravenous splint cover that simultaneously secures an IV site so as to prevent any need for reinsertion of an IV. Finally, a need exists for an intravenous splint cover that covers and protects the IV site, remains in place yet allows a medical professional or other person to view the IV site when desired without damaging the device or requiring the device's removal.

The devices described above, and other devices that may be known in the art generally suffer from the same deficiency, i.e., the devices prevent the patient from being able to move their extremity. Such restriction on movement also interferes with activities of daily living of the patient and immobilizes an area decreasing circulation and/or impeding blood flow. Patients that are uncomfortable while receiving IV treatments may not respond as well to treatment as patients who are comfortable.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a cannulated tube protector including a main body, a first pair of securing members extending distally from the main body, a second pair of securing members extending distally from the main body, and a splinting member with a viewing door. The viewing door may be structured to open thereby exposing a viewing aperture, defined as a doorway. The doorway may extend from a first surface of the main body to an opposing second surface of the main body.

In this embodiment, the splinting member may extend distally from the main body to create an elevated splinting member portion and the doorway may include at least one perforated sections of the elevated splinting member portion. The viewing door may include a thickness equal to the thickness of the elevated splinting member and may include at least one latch structured to facilitate opening the viewing door. The at least one latch may be structured to removably secure to the main body by at least one of adhesion, hook-and-loop fastener, snap, button, silicon, and clip.

In this embodiment, the splinting member may include a first elevated portion, defined as a platform, and a second elevated portion positioned on the platform. The platform may have at least one of a length and width greater than the second elevated portion creating at least one ledge between the platform and the second elevated portion. A section of the ledge may be structured as a side of the door attached to the main body. Furthermore, a side of the door attached to the main body may be operable as a hinge for the door. In some embodiments the platform and the second elevated portion may be a single unit.

Another embodiment may include an apparatus operable to facilitate the flow of fluids through a cannulated site including a main body, a first pair of securing members extending distally from the main body, a second pair of securing members extending distally from the main body and a splinting member with a rotatable viewing door. The splinting member may include one of a longitudinal and latitudinal profile with a bell curved frustum shape. Furthermore, at least one of the main body, the first pair of securing members, the second pair of securing members, and the splinting member may include a flexible material structured to be lifted to view an active intravenous site. Additionally, the viewing door may be structured to be opened to view an active cannulated site and may be at least one of square, rectangular, circular, oval, polygonal, and a combination thereof.

In some embodiments, the viewing door may be structured as a removeable segment taken from between the first pair of securing members. The viewing door may be configured to be removably secured to the main body via one of adhesion, hook-and-loop fastener, snap, button, silicon, and clip.

In this embodiment, the splinting member may include a first elevated portion, defined as a platform, and a second elevated portion positioned on the platform. The platform may have a longitudinal length that is greater than a longitudinal length of the second elevated portion. Additionally, the latitudinal length of the platform may be equal to the latitudinal length of the second elevated portion.

Other embodiments may include the splinting member with a first elevated portion, defined as a platform, and a second elevated portion positioned on the platform. The platform may have a latitudinal length that is greater than a latitudinal length of the second elevated portion. The longitudinal length of the platform may be equal to the longitudinal length of the second elevated portion.

One embodiment may include an apparatus operable to protect and maintain positioning of an IV catheter including a main body, a first securing member extending distally from the main body, a second securing member extending distally from the main body, and a splinting member comprising a viewing door.

The viewing door may be structured to open thereby exposing a viewing aperture, defined as a doorway. The doorway may extend from a first surface of the main body to an opposing second surface of the main body and may include a latch structured to facilitate opening the viewing door.

In this embodiment the splinting member may include a first elevated portion, defined as a platform, and a second elevated portion positioned on the platform, and wherein the platform has a latitudinal length that is greater than a latitudinal length of the second elevated portion; and wherein the longitudinal length of the platform is equal to the longitudinal length of the second elevated portion.

Additionally, the splinting member comprises a first elevated portion, defined as a platform, and a second elevated portion positioned on the platform; and wherein the platform has a latitudinal length that is greater than a latitudinal length of the second elevated portion; and wherein the longitudinal length of the platform is equal to the longitudinal length of the second elevated portion.

BRIEF DESCRIPTION OF THE DRAWINGS

FIG. 5 is a right-side elevation view of the intravenous splint cover illustrated in FIG. 1.

FIG. 6 is a left-side elevation view of the intravenous splint cover illustrated in FIG. 1.

FIG. 7 is a front elevation view of the intravenous splint cover illustrated in FIG. 1.

FIG. 8 is a rear elevation view of the intravenous splint cover illustrated in FIG. 1.

DETAILED DESCRIPTION OF THE INVENTION

Figure 1:
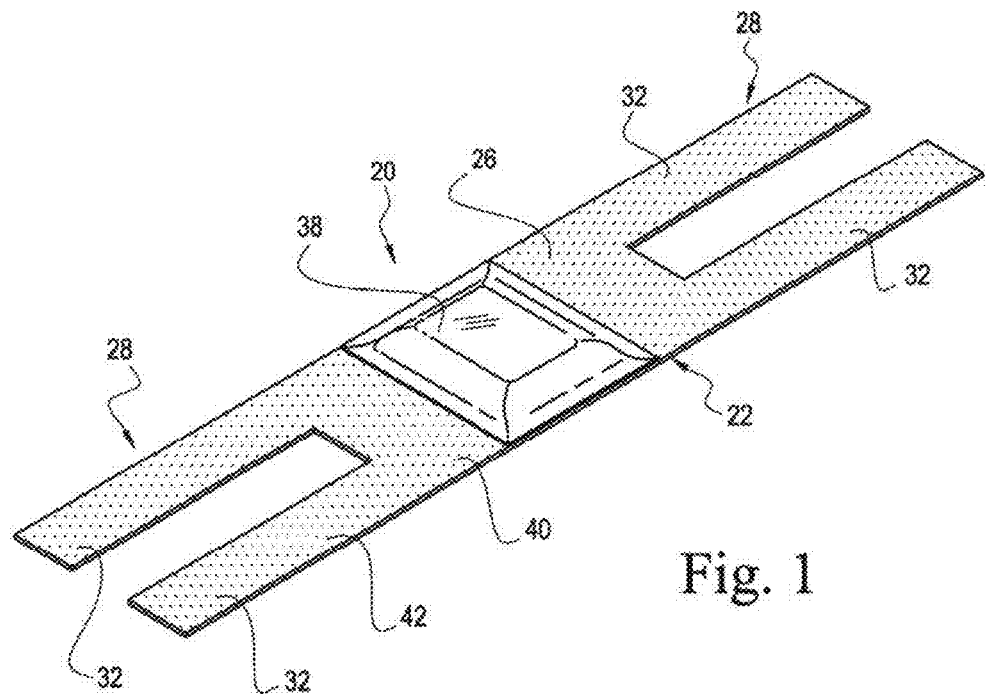
FIG. 1 is a bottom perspective view of an intravenous splint cover according to an embodiment of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Further, throughout this specification, the invention is referred to as an intravenous splint cover 20. Intravenous may sometimes be abbreviated as IV, and is not meant to be limiting in any way to the invention, as defined by the claims appended hereto. Throughout this disclosure, the intravenous splint cover 20 may be referred to as the IV splint cover, the splint cover, the system, the device, the apparatus or the invention. Alternate references to the intravenous splint cover 20 in this disclosure are not meant to be limiting in any way. Those skilled in the art will appreciate that an IV line 80, a line connected to a catheter 81, needle, cannula, flexible tube, etc. that is or has been inserted into a patient and is typically designed for IV therapy, may be positioned anywhere on a patient, including but not limited to any area and any body part, and, although the appended drawings illustrate an IV site 90 being positioned on an arm of a patient, the present invention advantageously may be used regardless of the positioning of the IV line 80 on the patient. The present invention is also not meant to be limited to use in connection with IV lines 80. Those skilled in the medical field will appreciate that the present invention can advantageously be used in connection with arterial lines and for dialysis lines, as well as other known treatments.

The IV site 90 includes the puncture area or wound area where the catheter 81, needle, cannula, flexible tube, etc. is inserted as well as the area of the skin over or above the inserted catheter 81, needle, cannula, flexible tube, etc. Once the catheter 81, needle, cannula, flexible tube, etc. is introduced into the vein (and often portions are removed, such as the needle from the catheter 81, cannula, flexible tube, etc.), the remaining portion remains in place for IV therapy. In the insertion process, the catheter 81, cannula, flexible tube, etc. may be over a needle or similar device. Once the needle or similar device and catheter 81, cannula, flexible tube, etc. are inserted into a vein or artery, the needle may be removed and the catheter 81, cannula, flexible tube, etc. may be left in place for IV therapy. An end hub of the catheter 81, cannula, flexible tube, etc. may then be connected to the IV line 80 which may have an extension with a port on the end that may be accessed for Intravenous fluid delivery. The IV site 90 may then be covered by a clear or transparent sterile dressing which may leave the extension and port accessible for clinicians to deliver fluids for IV therapy.

The IV splint cover 20 may cover the IV site 90 entirely and additionally cover other areas near the IV site 90. For example, and without limitation, in addition to the IV site 90, the IV splint cover 20 may cover a remaining portion of the catheter 81, needle, cannula, flexible tube, etc. that is not inserted in the patient. As another example, and without limitation, in addition to the IV site 90, the IV splint cover 20 may cover a portion of the IV line 80. The IV site 90 may also include areas of the patient's skin adjacent to the catheter 81, needle, cannula, flexible tube, etc. As yet another example, and without limitation, the IV site 90 may include a flexible tube catheter, sterile occlusive dressing to cover the insertion point extending from the length of the cannula to the extension set IV line 80, and an anchor or other stabilizing device. For example, and without limitation, the IV site 90 may include a flexible tube venous catheter in the vein covered by a sterile occlusive dressing to cover the insertion point extending from the length of the cannula to the extension set IV line 80 leaving the port on the end of the extension line accessible for fluid delivery and/or IV therapy.

The IV site 90 may also be described as comprising a catheter 81 or cannula which may also be called a flexible tube. A catheter hub may be connected to the IV line 80 which may also be called an extension tubing or a line. The IV site 90 may be covered by a clear or transparent sterile dressing. At the end of the IV line 80 the extension tubing may be a port for a clinician to access and deliver fluids to the patient for IV therapy.

Figure 2:
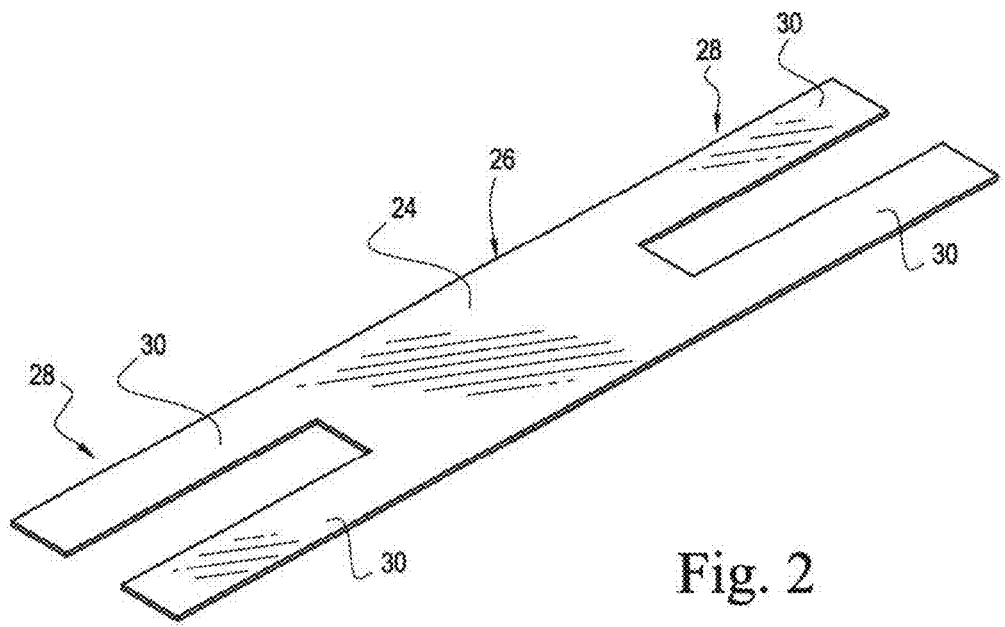
FIG. 2 is a top perspective view of the intravenous splint cover illustrated in FIG. 1.

Referring now to FIGS. 1 and 2, details of the intravenous splint cover 20 and methods according to an embodiment of the present invention are now discussed in greater detail. The intravenous splint cover 20 may include a main body 22. The main body 22 may be illustratively defined by a medial portion of the intravenous splint cover 20. As illustrated in FIGS. 1 and 2, the main body 22 of the intravenous splint cover 20 may include a bottom portion 26 and a top portion 24.

As further illustrated in FIGS. 1 and 2, the intravenous splint cover 20 may include a pair of opposing securing members 28 that are connected to and extend outwardly from the main body 22. Each of the pair of the opposing securing members 28 may also have a bottom portion 32 and a top portion 30. The intravenous splint cover 20 according to an embodiment of the present invention may also include a splinting member 38 that is carried by the bottom portion 26 of the main body 22. The splinting member 38 illustratively extends outwardly from the main body 22 of the intravenous splint cover 20 to create an elevated portion of the main body 22. More specifically, and with reference to FIG. 1, the splinting member 38 is also positioned along a medial portion of the main body 22 and, in the illustrated embodiment, along a medial portion of the IV splint cover 20. Those skilled in the art will appreciate, however, that the positioning of the splinting member 38 should not be limited to a medial portion of the IV splint cover 20 as it is contemplated that a length of the securing members 28 may differ. Additional details regarding the shape and positioning of the splinting member 38 and the securing members 28 of the IV splint cover 20 will be provided below.

The main body 22 and the securing members 28 of the IV splint cover 20 according to an embodiment of the present invention may advantageously be integrally formed as a monolithic unit. This advantageously enhances ease of manufacture, and decreases costs associated with manufacture. Those skilled in the art will appreciate, however, that the IV splint cover 20 according to the present invention may advantageously be manufactured by connecting the securing members 28 to the main body 22 so that the securing members 28 and the main body 22 are separate structural members that are joined together. The description of the IV splint cover 20 being integrally formed as a monolithic unit should not be read as limiting, but is meant to illustrate one advantageous configuration of the present invention.

In one embodiment of the IV splint cover 20 according to the present invention, the bottom portions 32 of the pair of opposing securing members 28 may have an adhesive material 42 applied thereto. Similarly, the bottom portion 26 of the main body 22 that does not carry the splinting member 38 may have an adhesive material 40 applied thereto. It is important for the reader to appreciate that the embodiment of the IV splint cover 20 of the present invention that uses the adhesive 40, 42 in connection with the main body 22 and the securing members 28 does not have any adhesive applied to the bottom portion 26 of the main body 22 where the splinting member 38 is positioned over the IV site 90. This advantageously allows for the IV site 90 to be readily visualized by a medical professional, for example, or anyone that may have a need to visualize the IV site 90 on the patient. This is also advantageous to enhance comfort of the patient while the IV splint cover 20 according to an embodiment of the present invention is applied to the patient. More specifically, removal of the IV splint cover 20 from the extremity of the patient upon completion of the IV treatment may be made more comfortable when an adhesive is not included on the splinting member 38. Additional details regarding the advantages of being able to readily visualize the IV site 90 of the patient when using the IV splint cover 20 according to embodiments of the present invention are discussed below.

Figure 13:
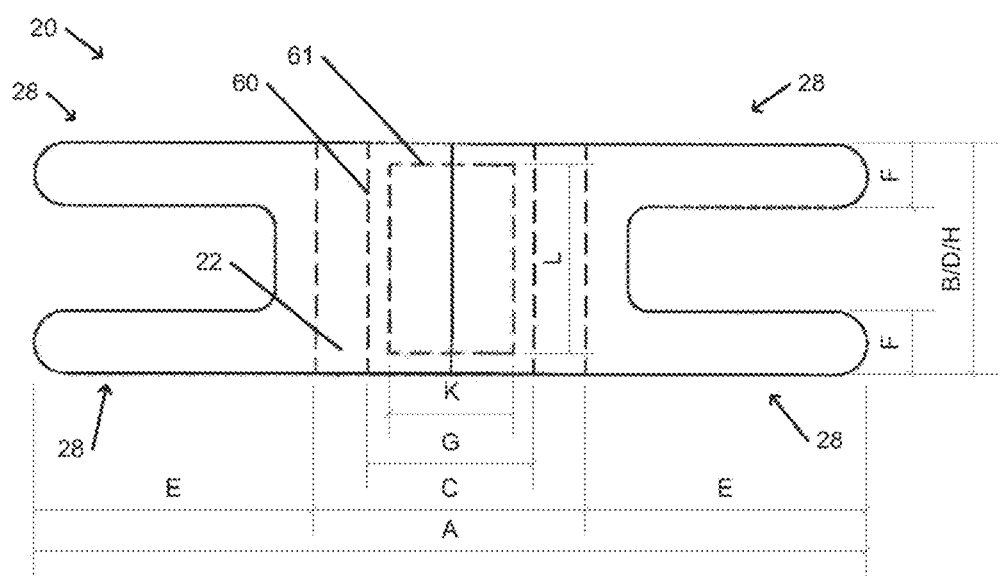
FIG. 13 is another bottom plan view of the intravenous splint cover illustrated in FIG. 1.
Figure 14:
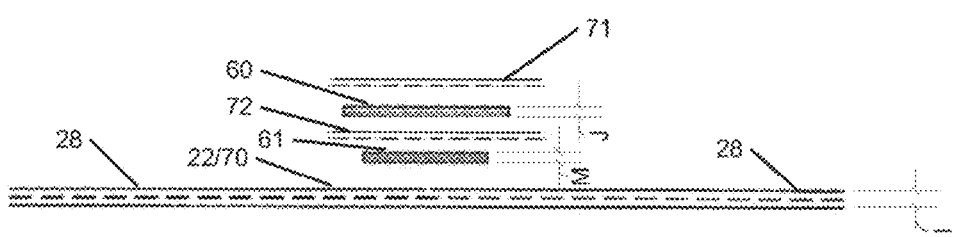
FIG. 14 is a side elevation view of the intravenous splint cover illustrated in FIG. 13.
Figure 15:
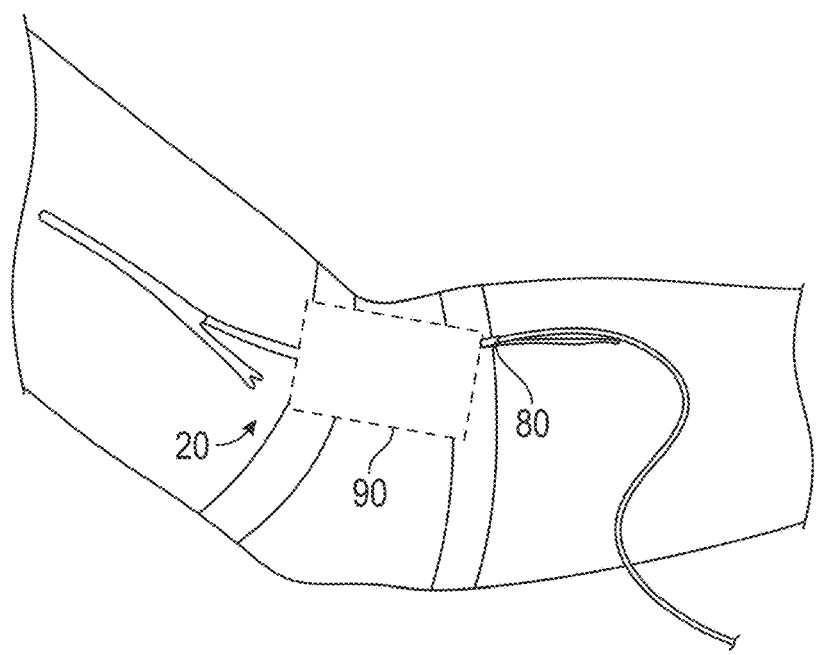
FIG. 15 is an environmental view of the intravenous splint cover illustrated in FIG. 1 positioned over an intravenous site on an extremity of a patient wherein the patient's extremity is straight.
Figure 16:
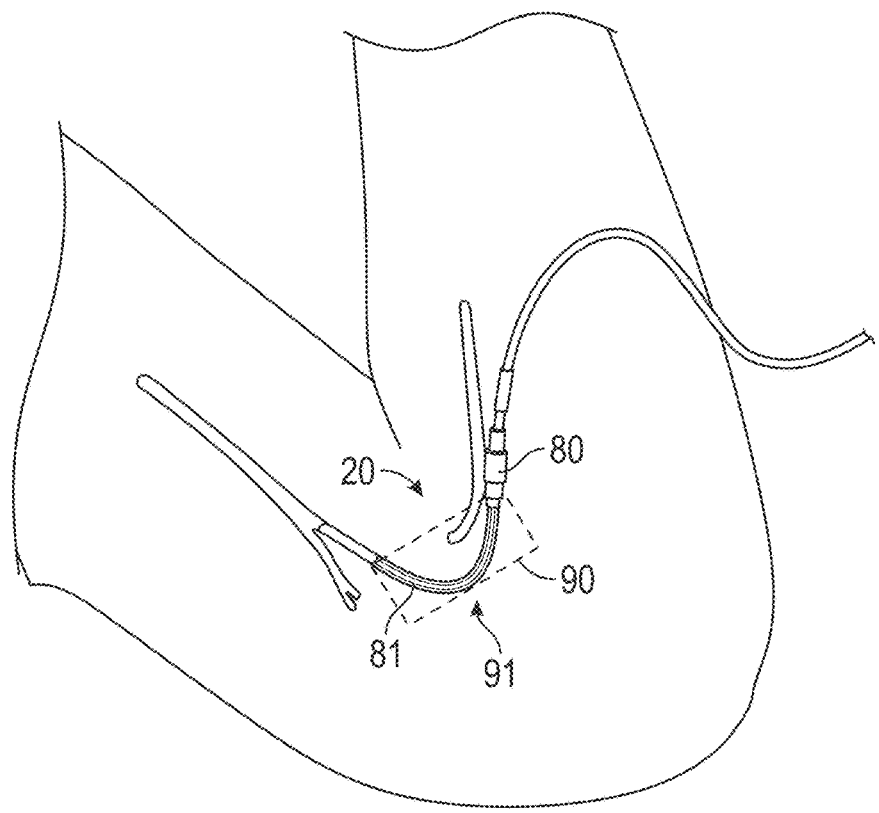
FIG. 16 is an environmental view of the intravenous splint cover illustrated in FIG. 1 as it is being positioned over an intravenous site on an extremity of a patient illustrated in a transparent fashion to show the patient's extremity being bent.
Figure 17:
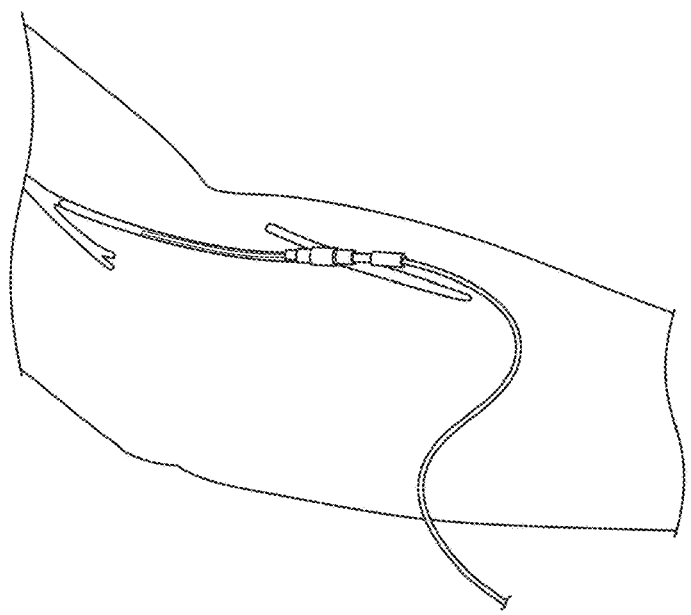
FIG. 17 is an environmental view of the intravenous site and an extremity of a patient without the intravenous splint cover wherein the patient's extremity is straight according to the prior art.
Figure 18:
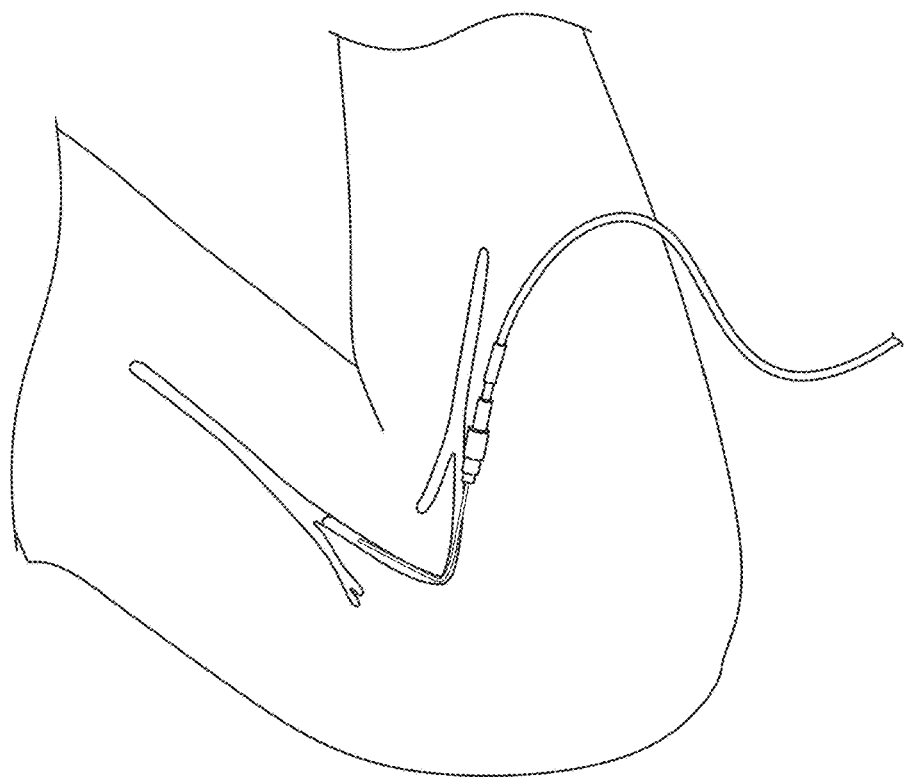
FIG. 18 is an environmental view of the intravenous site and an extremity of a patient without the intravenous splint cover wherein the patient's extremity is bent according to the prior art.

Referring now more specifically to FIGS. 13 and 14, the adhesive 40 may be applied to the main body 22 and may also allow the splinting member 38 to be secured to the main body 22. Additionally, the main body 22 may include a first and second main body 70, 71. The splinting member 38 may be placed on the first main body 70 and the second main body 71 may be placed on the splinting member 38. The adhesive 40 may be used to secure the splinting member 38 to the first main body 70 and the second main body 71 to the splinting member 38 and/or the first main body 70. The adhesive 40 may be used to secure the splinting member 38 and/or the first and/or second main body 70, 71 to each other or as otherwise desired. Those skilled in the art will appreciate that any number of methods, materials, and/or devices may be used to secure the splinting member 38 and/or the first and/or second main body 70, 71 including, but not limited to, adhesives, stitching or sewing, glue, fasteners, screws, bolts, welding (including ultrasonic welding), or any other means.

The adhesive material 42 that may be applied to the bottom portions 32 of the securing members 28 may have stronger adhesive properties than the adhesive material 40 that is applied to the bottom portion 26 of the main body 22. This may advantageously enhance the ability of the IV splint cover 20 to be readily secured to the IV site 90 on the patient. More specifically, providing a stronger adhesive on the securing members 28 may advantageously allow for the securing members to be readily secured to the skin of the patient when using the IV splint cover 20 according to an embodiment of the present invention. Further, using an adhesive 40 on the portion of the main body 22 (the portion that does not include the splinting member 38) that is weaker than the adhesive 42 used on the securing members 28 may advantageously enhance comfort of the patient when the IV splint cover 20 is applied to the IV site 90. In other words, when removing the IV splint cover 20, a patient may experience less discomfort adjacent to the IV site through the use of a weaker adhesive on the portions of the main body 22 where the splinting member 38 is not positioned.

Figure 3:
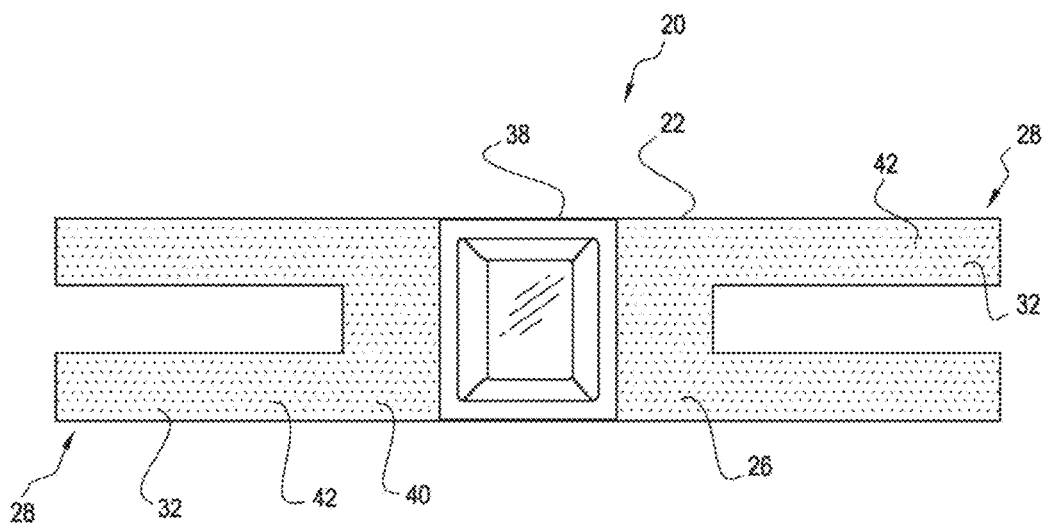
FIG. 3 is a bottom plan view of the intravenous splint cover illustrated in FIG. 1.
Figure 4:
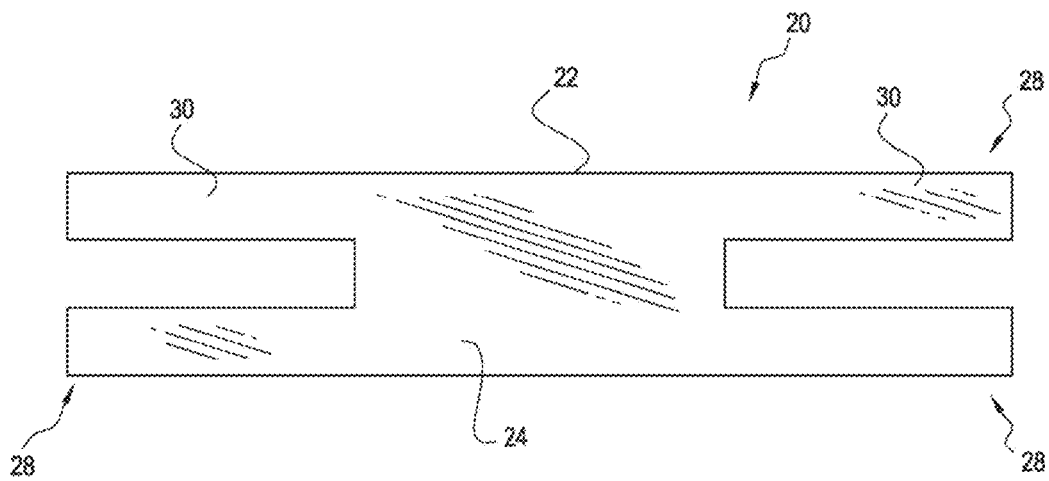
FIG. 4 is a top plan view of the intravenous splint cover illustrated in FIG. 1.
Figure 9:
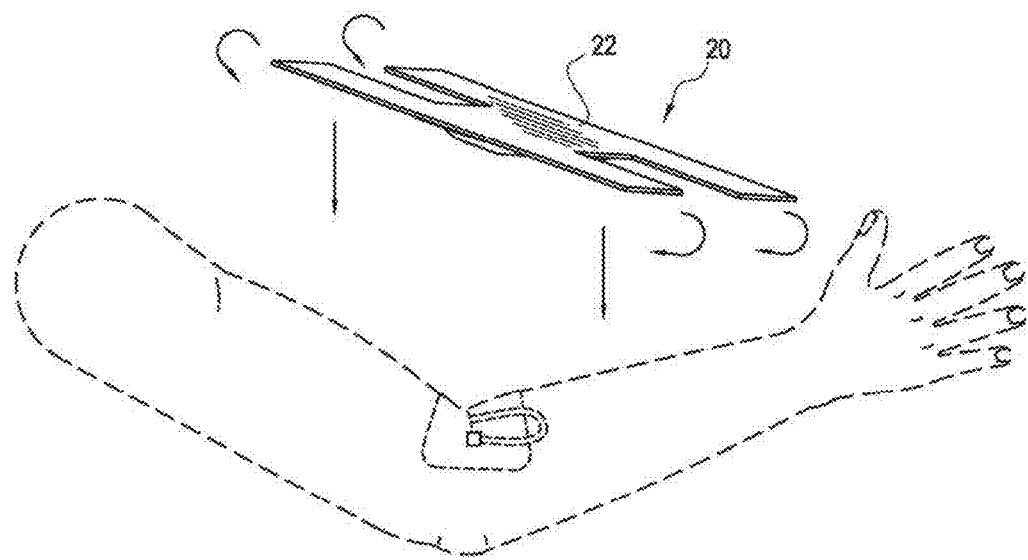
FIG. 9 is an environmental view of the intravenous splint cover illustrated in FIG. 1 as it is being positioned over an intravenous site on an extremity of a patient.

The splinting member 38 may extend along the bottom portion of the main body 22 substantially between the entire width thereof. More specifically, and as perhaps best illustrated in FIGS. 1 and 3, substantially the entire splinting member 38 may extend the entire width of the main body 22, but the elevated portion of the splinting member 38 may taper from an elevation that is about equal to or higher than the bottom portion 26 of the main body 22, to a pinnacle thereof. Accordingly, and as perhaps best illustrated in FIG. 1, the splinting member 38 may advantageously taper downwardly from the pinnacle to the main body 22 on four sides in a trapezoidal shape. Those skilled in the art will readily appreciate, however, that any description of the shape of the splinting member 38 is not meant to be limiting in any way and, instead, are provided as examples for clarity. The splinting member 38 may have a rectangular shape, as shown in the figures. A rectangular shaped splinting member 38 may advantageously be easy to manufacture and package, and may provide enhanced convenience in storing and transporting, i.e., in boxes and with respect to shelf space. A rectangular shaped splinting member 38 may also be advantageous to overlap with an IV site 90 plastic cover. Such covers are generally clear, and have a rectangular shape. Other alternate shapes of the splinting member 38 may, for example, be circular, square, ovular, or any other type of shape suitable for being carried by a medial portion of the main body 22.

As best illustrated in FIGS. 13-14 (not necessarily drawn to scale), the IV splint cover 20 may vary in size due to several factors, including, but not limited to, the size of the patient, the sex of the patient, the age of the patient, and the type of extremity or body part that the device will be adhered to on the patient. For example, and without limitation, the overall length of the IV splint cover 20 "A" including the securing members 28 and the main body 22, may be approximately 3.0 to 16.0 inches and preferably about 10 inches. The overall width of the IV splint cover 20 "B" may be approximately 15-50% of the overall length of the IV splint cover 20 and preferably about 2.75 inches. The length of the main body 22 "C" may be approximately 0.5 to 6.0 inches and preferably about 3.25 to 4.25 inches. The width of the main body 22 "D" may be about equivalent to the overall width of the IV splint cover 20. The length of each securing member 28 "E." may be approximately 5-25% of the overall length of the IV splint cover 20 and preferably about 2.875 inches. The width of each securing member 28 "F" may be approximately 15-50% of the overall width of the IV splint cover 20 and preferably about 0.75 inches. The length of the splinting member 38 "G" may be approximately 0.5 to 6.0 inches and preferably about 1.5 to 2.0 inches. The width of the splinting member 38 "H" may be approximately 15-50% of the overall length of the IV splint cover 20 and preferably about 2.25 to 2.75 inches. The thickness of the main body 22 and the securing members 38 materials "I" may be approximately 0.005 to 0.25 inches and preferably about 0.011 inches. The thickness of the splinting member 38 "J" may be approximately 0.0625 to 1.0 inches and preferably about 0.125 inches. Those skilled in the art will appreciate that these dimensions may be increased or decreased as desired and the dimensions stated herein provided are exemplary.

For example and without limitation, some of the lengths, widths, and/or thicknesses may be substantially similar to one another. Substantially similar may indicate that the first measurement may be within a range of 80% to 120% of the second measurement. In addition, some of the lengths, widths, and/or thicknesses may be about a measurement. About may indicate that the actual measurement may be within a range of 80% to 120% of the specific measurement.

The splinting member 38 may be made of a substantially soft and pliable material. For example, the splinting member 38 may include a foam type of material, a cotton splint material, a plastic material, a metallic material, a metal-alloy material, a ceramic material, a polymer material, other similar material, or any combination thereof. For example, and without limitation, the splinting member 38 may be a crosslinked polyethylene foam coated on one side with an acrylic based, hypoallergenic pressure sensitive adhesive. The acrylic and/or stretchable based, porous, breathable, and/or hypoallergenic pressure sensitive adhesive may be protected by a polycoated white kraft release liner. Cotton materials may be preferable to form the splinting member as it may provide enhanced rigidity, and may be more suitable for patients that have allergies to various materials. The use of such material advantageously enhances comfort of the IV splint cover 20 when applied to the IV site 90 of the patient. Such material may also advantageously have certain absorption properties that can be advantageous to soak minor amounts of blood, fluid, or medication leaks that may be associated with the use of an IV. Comfort of the patient is one of the several advantages provided by the IV splint cover 20 according to the present invention, and those skilled in the art will appreciate that the splinting member 38 may be made of any other similar material that provides enhanced comfort to the patient when applied to the IV site 90. In addition, the splinting member 38 material may be more rigid than the main body 22 material and/or the securing members 28 material.

The splinting member 38 may include a first splinting member 60 and a second splinting member 61. The first splinting member 60 may include a foam type of material, a cotton material, a plastic material, a metallic material, a metal-alloy material, a ceramic material, a polymer material, other similar material, or any combination thereof. The first splinting member 60 may preferably be a cotton material such as a nonwoven tape. The second splinting member 61 may include a foam type of material, a cotton material, a plastic material, a metallic material, a metal-alloy material, a ceramic material, a polymer material, other similar material, or any combination thereof. The second splinting member 61 may preferably be a foam type of material. For example, and without limitation, the second splinting member 61 may be a crosslinked polyethylene foam coated on one side with an acrylic based, hypoallergenic pressure sensitive adhesive. The acrylic based, hypoallergenic pressure sensitive adhesive may be protected by a polycoated white kraft release liner.

The second splinting member 61 may attach to the main body 22. The first splinting member 60 may attach to the main body 22 and/or the second splinting member 61. The first splinting member 60 may be larger than the second splinting member 61. For example and without limitation, the first splinting member 60 may be about 2.0 inches long and about 2.750 inches wide and the second splinting member 61 may be about 1.5 inches long and about 2.25 inches wide.

The adhesive 40 may be applied to the main body 22 and may also allow the first and second splinting members 60, 61 to be secured to the main body 22. The main body 22 may include, in addition to the first and second main body 70, 71, a third main body 72. The second splinting member 61 may be placed on the first main body 70, the third main body 72 may be placed on the second splinting member 61 and/or the first main body 70, the first splinting member 60 may be placed on the third main body 72, the second splinting member 61, and/or the first main body 70, and the second main body 71 may be placed on the first splinting member 60, the third main body 72, the second splinting member 61, and/or the first main body 70. The adhesive 40 may be used to secure the first and/or second splinting member 60, 61 and/or the first, second, and/or third main body 70, 71, 72 to each other or as otherwise desired. Those skilled in the art will appreciate that any number of methods, materials, and/or devices may be used to secure the first and/or second splinting member 60, 61 and/or the first, second, and/or third main body 70, 71, 72 including, but not limited to, adhesives, stitching or sewing, glue, fasteners, screws, bolts, welding (including ultrasonic welding), or any other means.

As best illustrated in FIGS. 13-14, the length of the first splinting member 60 "G" may be approximately 0.5 to 6.0 inches and preferably about 2.0 inches. The width of the first splinting member 60 "H" may be approximately 15-50% of the overall length of the IV splint cover 20 and preferably about 2.75 inches. The thickness of the first splinting member 60 "J" may be approximately 0.0625 to 1.0 inches and preferably about 0.125 inches. The length of the second splinting member 61 "K" may be approximately 0.5 inches to 6.0 inches and preferably about 1.5 inches. The width of the second splinting member 61 "L" may be approximately 15-50% of the overall length of the IV splint cover 20 and preferably about 2.25 inches. The thickness of the second splinting member 61 "M" may be approximately 0.0625 to 1.0 inches and preferably about 0.125 inches. Those skilled in the art will appreciate that the length of the first and second splinting members 60, 61 may be equal to the full length of the main body 22. The width of the first and second splinting members 60, 61 may be equal to the full width of the main body 22.

As perhaps best illustrated in FIG. 1, each of the pair of opposing securing members 28, i.e., each of the securing members 28 on either side of the main body 22 of the IV splint cover 20, may include a pair of securing members 28. More specifically, and with specific reference to FIGS. 1 and 2, the securing members 28 may be spaced apart from one another and extend outwardly from the main body 22 substantially parallel to one another. The securing members 28 on either end of the main body 20 may be considered symmetrical to one another. The present invention contemplates, however, that the securing members 28 on either end of the main body 22 of the IV splint cover 20 may have different lengths or may have similar lengths. Application of the of the IV splint cover 20 may, in some instances be facilitated if the securing members 28 on one end of the main body 22 have a length that is greater than the securing members 28 on the opposing end of the main body 22. Again, this may be an optional feature, and the skilled artisan will appreciate that any length of the securing members 28 of the IV splint cover 20 according to an embodiment of the present invention is contemplated by the present invention.

Although the embodiment of the IV split cover 20 illustrated in the appended figures shows the use of a pair of securing members 28 on either side of the main body 22, those skilled in the art will appreciate that any number of securing members 28, configured in any way, may be provided while still carrying out the many different goals, features and advantages according to the present invention. For example, the illustrated embodiment of the IV splint cover 20 shows a pair of securing members 28 extending parallel to one another outwardly from each side of the main body 22, but those skilled in the art will appreciate that the securing members 28 do not need to necessarily extend parallel to one another out from the main body 22. In fact, the securing members 28 may extend in any direction, e.g., diagonally. Further, although a pair of securing members 28 is illustrated on either side of the main body 22, the present invention contemplates that more than two securing members 28 may be used to carry out the many different goals and features of the present invention. More specifically, it is contemplated that three securing members 28 may extend outwardly from the main body 22 of the IV splint cover 20. Such a configuration may advantageously provide enhanced security of the IV splint cover 20 according to the present invention when applied to the IV site 90 of a patient. It should be noted, however, that the illustrated embodiment of the IV splint cover 20 does advantageously provide for enhanced security of the IV site 90 of the patient while simultaneously providing the patient with ease of mobility of the extremity where the IV site 90 is positioned. For example and without limitation, if the catheter 81, needle, cannula, flexible tube, etc. is or has been inserted in the cubital fossa, also known as the elbow pit or antecubital fossa, the IV splint cover 20 may allow a patient to bend, or bend further, his or her arm at the elbow. With the IV splint cover 20 in place, damage to the patient caused by bending of the arm of the patient may be reduced or negated. With the IV splint cover 20 in place, kinking, shifting, dislodging or blockage of the IV line 80 may be reduced or negated, thus allowing for continued IV therapy 91. Thus, the patient may have increased mobility when the IV splint cover 20 is used as opposed to when the IV splint cover is not used. For example and without limitation, the wrist may be able to bend and the forearm may be able to rotate and/or pivot as desired when the IV splint cover 20 is attached to the wrist and forearm, respectively.

The material that the IV splint cover 20 according to an embodiment of the present invention may be made of, i.e., the main body 22 and the securing members 28, may be a disposable material that is preferably biodegradable. Such materials are readily known in the art. For example and without limitation, the main body 22 and securing member 38 materials may be polyurethane and the adhesive materials 40, 42 may be acrylate. Using such material is advantageous to reduce waste. Those skilled in the art will appreciate that the main body 22 and the securing members 28 of the IV splint cover 20 may, however, be made of any type of material, while still readily achieving the many different goals and features according to the present invention. It is also preferable that the material of the IV splint cover 20 be substantially flexible with at least some rigidity and/or stretchability. Using such material enhances application of the IV splint cover 20 to the IV site 90 of the patient. As will be discussed in greater detail below, application of the IV splint cover 20 to the IV site 90 of the patient can be accomplished in a one step process. This one step process is enhanced when using a flexible and/or stretchable material to form the main body 22 and the securing members 28 of the IV splint cover 20.

It is also preferable that all material used to construct the IV splint cover 20 according to the present invention is made of a pressure sensitive, porous, breathable and/or hypoallergenic material. Although it is readily understood that constructing the IV splint cover 20 out of such material may be a more costly approach, it is preferable to provide an IV splint cover that can be readily used for all patients. Those skilled in the art, however, will appreciate that the IV splint cover 20 may be readily made of any material, and that use of a hypoallergenic material is an available option contemplated by the present invention. The IV splint cover 20 according to the present invention may also be made of a latex free material to further account for possible allergies of a patient. Again, those skilled in the art will appreciate that any material may be used to construct the IV splint cover 20, but the present invention readily contemplates use of such materials to account for possible allergies that patients may have. Although many patients may be allergic to certain types of materials, the present invention contemplates using paper types of materials to construct the IV splint cover 20.

The material that may be used to construct the IV splint cover 20 may also have a color that is similar to the skin tone of the patient. This is advantageous for many reasons. Although it may seem that having an IV splint cover 20 with a color that is similar to the skin tone of the patient is merely aesthetic, those skilled in the art will appreciate that using an IV splint cover 20 having a color similar to the skin tone of the patient is advantageous as it can hide the IV splint cover from view of the patient. This may be especially advantageous when using the IV splint cover 20 on patients that may be easily confused. Such patients may desire to rip the IV out, and use of the IV splint cover 20 according to the present invention may hide the IV from site of such patients, thereby detracting attention from it.

A portion of the IV splint cover 20 may be lifted so that a medical professional may view the IV site 90, the catheter 81, needle, cannula, flexible tube, etc., or the IV line 80, or any portion thereof, without the need for removing the IV splint cover 20. For example and without limitation, the splinting member 38 and the top portion 24 may be lifted so that the IV site 90 or a portion thereof may be viewed. The bottom portions 32 of the securing members 28 may remain adhered to the patient while the splinting member 38 and the top portion 24 are lifted. The ability to stretch, lift, view, and/or assess a portion of the IV splint cover 20 will keep the IV site 90 covered so that a patient still cannot view the IV site 90, the catheter 81, needle, cannula, flexible tube, etc., or the IV line 80, or portions thereof, yet still allow a medical professional to view the IV site 90, the catheter 81, needle, cannula, flexible tube, etc., or the IV line 80, or any portion thereof, when desired or necessary. For example and without limitation, a user may grasp a center portion of the splinting member 38, which may be non-adhesive, with fingers to stretch, lift, view, and/or assess the IV site 90. Once the splinting member 38 is released, it may return to its previous form and may keep the IV site 90 covered so that a patient cannot view the IV site 90, the catheter 81, needle, cannula, flexible tube, etc., and/or at least a portion of the IV line 80.

Thus, the IV site 90 may remain accessible to a user to be able to assess, palpate, and visualize the IV site 90 at any time. The IV site 90 may be easily viewed or palpated from the top or bottom without removing the IV splint cover 20. The IV splint cover 20 may remain on the patient over the IV site 90 without the splinting member 38 adhering to or removing the existing intact IV site 90. For example, and without limitation, to view the insertion site and/or the IV site 90 a user may grasp a portion of the IV splint cover 20, such as the splinting member 38, by lifting the portion of the IV splint cover 20 along the side edge of the IV splint cover 20. As another example, and without limitation, a user may lift and stretch a portion of the IV splint cover 20 from the top edge or bottom edge of the splinting member 38. These examples may allow a user to view or palpate the IV site 90 underneath the IV splint cover 20 as desired. The IV splint cover 20 may stretch by lifting, but may return to its original form or generally its original form to conform to the IV site 90 allowing the splint cover 20 to return to the function of allowing mobility of the patient's extremity by splinting the IV site 90 and preventing kinking, shifting, blocking, damage or dislodgement of the catheter 81, needle, cannula, flexible tube, etc. Thus, the patient may be free or freer to move his or her extremity or joint to completely pivot and continue pivoting during IV therapy 91 without the need for immobilization of a joint or extremity.

Furthermore, the IV site 90 may be easy to visualize, access, and/or palpate without compromising the IV site 90 while protecting it underneath as the IV splint cover 20 remains intact over the IV site 90. By further preserving the IV site 90, users may be less invasive and the risk of introduction of infection from IV reinsertion may be reduced. The IV splint cover may be applied in a one step process and may be easy to use, comfortable, hypoallergenic, camouflaging, inexpensive to make, disposable, and environmentally friendly.

The IV splint cover 20 may be made of a material that is flexible and/or capable of stretching so that when the IV splint cover 20, or a portion thereof, is lifted, the IV splint cover 20 may generally maintain its position, shape, and/or size. This flexibility may allow the IV splint cover 20 to retain its form for support and continue to allow a patient to have mobility in his or her extremities.

At least a portion of the IV splint cover 20 is made of a stretch material allowing for flexibility and bending. The splinting member 38 may be an elevated cushion pad in the center of the IV splint cover 20 which is designed to splint, support and protect the catheter 81, needle, cannula, flexible tube, etc. The splinting member 38 may have the ability to stretch, but maintain enough rigidity and retain or nearly retain its form for splinting the IV site 90 with the ability to allow complete or nearly complete movement and pivoting when a joint or extremity moves Application of the IV splint cover 20 may be accomplished by pulling a pair of adhesive cover members 44 and applying one self-adhesive side at a time in one motion with the splinting member 38 centered over the IV site 90. The two securing members 28 may adhere to the patient's skin on each end parallel to each other and may wrap around the extremity or joint adhering to the skin and allowing for the extremity or joint to have free or generally free range of motion. Once applied, the securing members 28 may stretch with the extremity or joint when the extremity or joint moves and may work together with the stretch ability of the splinting member 38. The IV splint cover 20 may be used on all patients. By covering, protecting, and splinting the IV site 90, a user may have more comfort and the IV site 90 may be concealed from the patient's view which may be especially beneficial to patients who are needle-phobic, infants, children, confused, and/or agitated patients while still allowing the ability for total joint or extremity flexion, IV site 90 access, and IV therapy 91.

The securing members 28 may be applied above and below the joint to allow bending of any joint by stretching with the joint and or extremity when the joint or extremity moves. A user may pull the pair of adhesive cover members 44 in one motion allowing the securing members 28 to adhere to the patient's skin. When the securing members 28 are wrapped around a joint or extremity, the securing members 28 may contour above and below the joint which may allow for bending and flexibility of the extremity or joint. The securing members 28 may overlap on the ends but do not need to overlap to allow a patient to move and bend more freely. The placement and ability of the securing members 28 to stretch yet retain their form by conforming to an extremity or joint may help to promote blood flow without causing a tourniquet effect. Once the securing members 28 are applied to the joint or extremity, the joint or extremity may bend while the securing members 28 may stretch and may allow for continued mobility and pivoting of an extremity or joint and thus allowing movement without the need for immobilizing of the joint or extremity which may otherwise impede blood flow and circulation.

It may also be advantageous to provide a material for the main body 22 and the securing members 28 that is waterproof or water resistant. This advantageously allows a patient to bath or shower while the IV splint cover 20 is applied to the IV site 90. Accordingly, the IV splint cover 20 according to embodiments of the present invention not only allows the patient's extremity to remain mobile while in use, but also advantageously enhances the ability of the patient to engage in other routine daily activities while IV medical treatments are being administered. Further, the IV splint cover 20 is advantageous for patients that are receiving multiple IV treatments, i.e., use of the IV splint cover prevents immobilization of the patient's extremities, which can be especially advantageous for patients that may have IV's in two different extremities.

Figure 10:
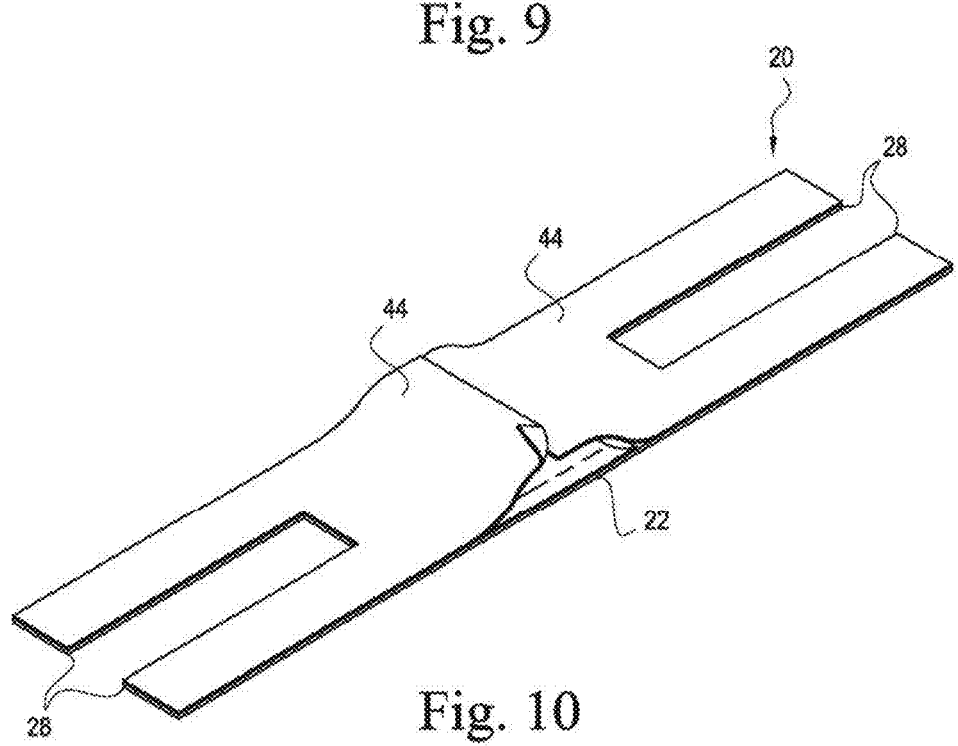
FIG. 10 is a perspective view of an intravenous splint cover according to an embodiment of the present invention showing a pair of adhesive cover-members positioned over a bottom surface portion thereof.

As perhaps best illustrated in FIG. 10, the IV splint cover 20 according to the present invention may further include adhesive cover members 44 that may be removeably positioned over the main body 22 and the securing members 28. The adhesive cover members 44 are positioned to overlie the bottom portion 26 of the main body 22 and the bottom portion 32 of the securing members 28. Accordingly, the adhesive cover members 44 may readily protect the adhesive from exposure when not in use to ensure that the adhesive remains strong enough to be applied to a patient. As further illustrated in FIG. 10, the adhesive cover members 44 may be provided by a pair of adhesive cover members 44. A first one of the pair of adhesive cover members 44 may be positioned to extend from an end portion of one of the securing members 28 to a medial portion of the main body 22 of the IV splint cover 20, and a second one of the pair of adhesive cover members 44 may extend form an end portion of the opposing securing member 28 to the medial portion of the main body 22. Accordingly, the present invention contemplates that end portions of the adhesive cover members 44 may somewhat overlap adjacent the medial portion of the main body 22 so that the adhesive cover members 44 can be readily removed when used.

The adhesive cover members 44 may be made of a paper material, a paper-like material, a paper material having a plastic coating, or a plastic material to cover the portions of the main body 22 and the securing members 28 that have adhesive material applied thereto. The use of such materials for the adhesive cover members 44 advantageously allows for the adhesive cover members 44 to be readily connected to the adhesive portions of the main body 22 and the securing members 28 in a manner that allows the adhesive to remain protected from the elements, and that allows for the adhesive cover members 44 to be readily removed from the adhesive portions of the IV splint cover 20.

Figure 11:
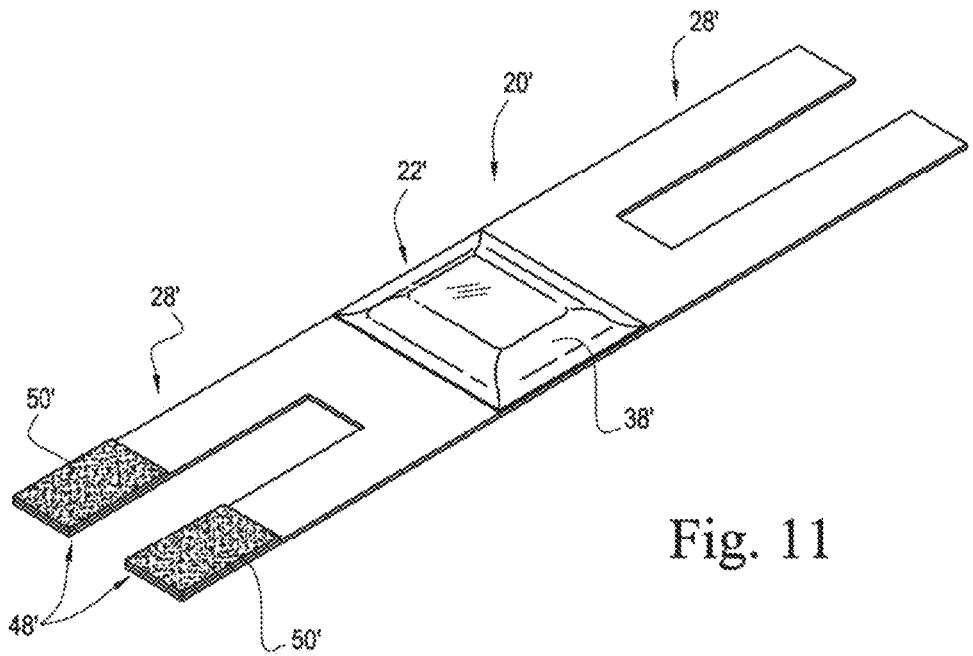
FIG. 11 is a perspective view of an intravenous splint cover according to an embodiment of the present invention.
Figure 12:
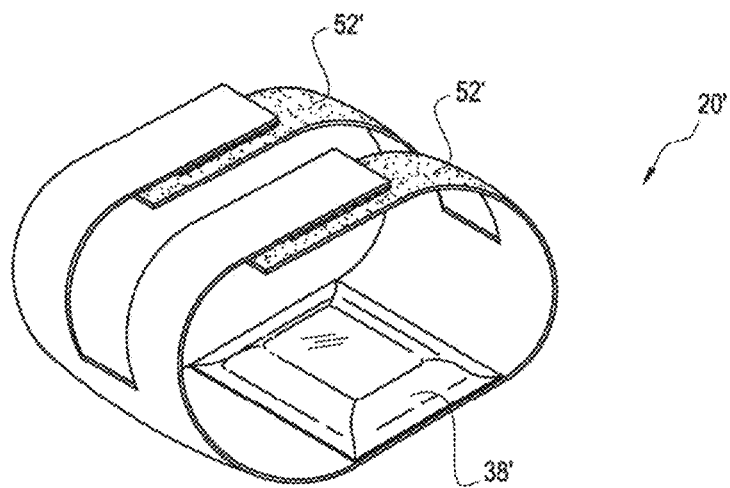
FIG. 12 is a perspective view of the intravenous splint cover illustrated in FIG. 11 showing securing members being connected to one another.

Referring now additionally to FIGS. 11 and 12, an alternate embodiment of the IV splint cover 20' is now discussed in greater detail. More specifically, the IV splint cover 20' may include a pair of opposing securing members 28' that are connected to and extend outwardly from the main body 22'. In this embodiment of the IV splint cover 20', fasteners 48' may be carried by end portions of each of the pair of securing members 28'. The fasteners 48' may include fasteners 50' positioned on the bottom side of the securing members 28' and fasteners 52' positioned on the top side of the securing members 28'. The fasteners 48' may be provided by hook and loop fasteners, as understood by those skilled in the art. The other elements of this embodiment of the IV splint cover 20' not specifically described herein are similar to those of the first embodiment of the IV splint cover 20 described above, are labeled with prime notations, and require no further discussion herein.

Referring now back to FIGS. 1 through 10, use of the IV splint cover 20 according to an embodiment of the present invention is now described in greater detail. When using the IV splint cover 20 according to an embodiment of the present invention, a user, such as, for example, a medical professional, may remove the IV splint cover 20 from a package. The packaging that contains the IV splint cover 20 is preferably a sterilized material to ensure that the IV splint cover 20 remains sterile during transport, however, the packaging and the IV splint cover 20 may not be sterilized or composed of sterilized material(s). The IV splint cover 20 may be sterile and therefore the material or materials that make up the IV splint cover 20 may also be sterile. This advantageously reduces the risk of infection to the patient when using the IV splint cover 20. Those skilled in the art will appreciate that although the packaging that houses the IV splint cover 20 is described herein, the function of the present invention can be readily carried out without the use of such packaging.

After the IV splint cover 20 according to the present invention has been removed from the packaging, the medical professional may remove the adhesive cover members 44 positioned to overlie the bottom portion 26 of the main body 22 and the bottom portion 32 of the securing members 28. Removal of the adhesive cover members 44 advantageously exposes the adhesive material 40, 42 positioned on the bottom portion 26 of the main body 22 and the bottom portion 32 of the securing members 28. Removal of the adhesive cover members 44 also advantageously exposes the splinting member 38. After the bottom portion of the main body 22 has been exposed, the medical professional may readily apply the IV splint cover 20 centered and/or over the IV site 90 of the patient. The securing members 28 may be adhered to the patient one side at a time with or without stretching. To inspect the IV site 90, the center portion of the splinting member 38, which may be non-adhesive, may be lifted to visualize the IV site 90.

Those skilled in the art will appreciate that the medical professional may completely remove the adhesive cover members 44 or may, alternatively, only remove enough of the adhesive cover members 44 to expose the splinting member 38. As described below, the securing members 28 can be applied directly to the skin of the patient adjacent to the IV site 90, if the adhesive cover members 44 are fully removed, or the adhesive cover members 44 can be removed as the securing members 28 are applied to the skin of the patient. In other words, the process of removing the adhesive cover members 44 and applying the securing members 28 to the skin of the patient can be a substantially simultaneous process. This advantageously allows for the adhesive material on the bottom portion 26 of the main body 22 and on the bottom portion 32 of the securing members 28 to remain covered until almost the instant that the main body 22 and the securing members 28 are to be applied to the IV site 90.

When applying the IV splint cover 20 to the IV site 90 of the patient, the medical professional, after starting the IV, may apply the splinting member 38 by centering it over the IV site 90. Application of the splinting member 38 to the IV site 90 may advantageously prevent the catheter 81, needle, cannula, flexible tube, etc. from bending when the patient bends their extremity. More particularly, the splinting member 38, after being applied over the IV site 90, keeps the catheter 81, needle, cannula, flexible tube, etc. from bending, but advantageously allows the extremity of the patient to bend, so that the patient can be comfortable while receiving IV treatments and can enjoy other routine daily activities. Thereafter, the securing members 28 may adhere in one motion, one side at a time over the extremity of the patient, and the adhesive material 40, 42 on the main body 22 and the securing members 28 may be applied to the skin of the patient. The splinting member 38 advantageously secures the IV site 90 so that the IV does not come out while the patient is receiving IV treatments. Further, application of the IV splint cover 20 to the extremity of the patient where the IV is located advantageously secures the IV while not immobilizing the patient's extremity. In other words, the patient may still readily move and bend the extremity where the IV is located while the IV remains secured while stretching with movement.

The configuration of the IV splint cover 20 according to embodiments of the present invention advantageously allows for application of the IV splint cover 20 in a one step process. This step can be described as simply applying the splinting member 38 to the IV site 90 by centering the splinting member 38 over the IV site 90 while connecting the securing members 28 to the skin of the patient adjacent to the IV site 90.

The configuration of the IV splint cover 20 according to the present invention also advantageously provides the medical professional with the ability to readily connect the IV splint cover 20 to the IV site 90 of the patient using one hand, which may sometimes be necessary in many medical settings. For example, after applying the splinting member 38 to the IV site 90 of the patient, the medical professional may hold the splinting member 38 securely on the IV site 90 using a thumb, fingers or hand, for example, and may move the securing members 28 over the side portions of the extremity (to either side of the IV site 90) so that the adhesive portions on the main body 22 of the IV splint cover 22 and on the securing members 28 contact the skin of the patient. After the IV splint cover 20 according to this embodiment of the invention is positioned over the IV site 90 of the patient, and since adhesive is not applied to portions of the main body 22 where the splinting member 38, which may be non-adhesive, is positioned and/or centered over the IV site 90, the IV site 90 may be readily visualized by the medical professional when the IV splint cover 20 is applied by grasping, for example, the top edge or bottom edge of the splinting member 38 with fingers then stretching and lifting the center portion of the splinting member 38 to assess and visualize the IV site 90.

It is preferable when applying the IV splint cover 22 to the IV site 90 on the patient, that the securing members 28 do not overlap one another at end portions thereof, however the securing members 28 may overlap one another at end portions thereof and may adhere to one another. More specifically, the medical professional may stretch the securing members 28 a distance suitable for the securing members 28 to overlap one another during application. Alternatively, the medical professional may place the securing members 28 on the skin of the patient with little or no stretching of the securing member 28. The securing members 28 may or may not overlap and may stretch upon movement of the patient, the patient's extremity, or otherwise as desired. It is also preferable for the securing members 28 to be applied to the skin of the patient adjacent the joint on the patient where the IV site 90 is positioned. This enhances mobility of the patient when the IV splint cover 20 is positioned over the IV site 90.

Referring now back to the embodiments of the IV splint cover 20' illustrated in FIGS. 11 and 12, another embodiment of the method of using the IV splint cover 20' is now described in greater detail. In this embodiment, the fasteners 48' positioned on the bottom portion of the securing members 50' and on the top portion of the securing members 52' may be configured to connect to one another. As described above, the fasteners 48' may be provided by hook and loop fasteners. Accordingly, and with reference to the illustrated embodiment of the IV splint cover 20', the securing members 28' that extend outwardly from a first side of the main body 22' may have fasteners 50' positioned on a bottom portion thereof, and the securing members 28' extending from the opposing side of the main body 22' may have fasteners 52' positioned on a top portion thereof. After the medical professional has applied the splinting member 38' to the IV site 90', the securing members 28' may be placed and/or stretched over the extremity of the patient, and the securing members 28' may be connected to one another so that the fasteners 48' may be connected to one another.

Some additional features of the IV splint cover 20 are now described in greater detail. One option that is contemplated by the present invention is to make the IV splint cover 20 child friendly. This can be accomplished by positioning indicia that is child related on the top portion of the main body 22 and the securing members 28. The indicia may, for example, be directed to children's characters, or any other type of indicia that may be pleasing to children. This advantageously directs children's attention away from the IV site 90, and may focus the children's attention on the characters that are printed on the IV splint cover 20. The IV splint cover 20 according to the present invention also contemplates that the main body 22 and securing members 28 may be very brightly colored, which may also detract a child's attention from the IV site 90.

The splinting member 38 may completely cover the IV site 90 or a portion of the IV site 90. For example, and without limitation, the splinting member 38 may be positioned over the inserted portion of the catheter 81, needle, cannula, flexible tube, etc. that is beneath the skin of the patient. As another example, and without limitation, the splinting member 38 may be positioned over the entire length of the catheter 81, needle, cannula, flexible tube, etc. including the inserted portion beneath the skin of the patient as well as the portion above the skin of the patient. The positioning of the splinting member 38 may prevent or aid in preventing the catheter 81, needle, cannula, flexible tube, etc. from bending, breaking, kinking, shifting or dislodging.

As another embodiment of the IV splint cover 20, a method of using the IV splint cover 20 may also be used. In the method, the IV splint cover 20 may include a main body 22 that may have a rectangular shape and may include a bottom portion 26 and a top portion 24. The IV splint cover 20 may further include a pair of opposing securing members 28 that may have a rectangular shape and may be connected to and may extend outwardly from the main body 22 and may include a bottom portion 32 and a top portion 30. The IV splint cover 20 may also include a splinting member 38 that may have a rectangular shape and may be carried by the bottom portion 26 of the main body 22 and may extend outwardly from the main body 22 to create an elevated portion of the main body 22. The IV splint cover 20 may yet further include a pair of adhesive cover members 44.

The method may include removing a portion of the pair of adhesive cover members 44 so that an adhesive side of one set of opposing securing members 28 and a portion of the main body 22 may be exposed. The method may further include positioning the splinting member 38 over an IV site 90 and securing the one set of opposing securing members 28 and the portion of the main body 22 to skin of a patient. The method may also include removing the opposing portion of the pair of adhesive cover members 44. The method may still further include securing the opposing set of opposing securing members 28 and the opposing portion of the main body 22 to another portion of the skin of the patient or to the set of opposing securing members 28. Those skilled in the art will appreciate that the methods herein may be performed in an interchangeable order. Further, those skilled in the art will appreciate that multiple adhesive cover members 44 may be removed at or near the same time, thus exposing the adhesive side of the securing members 28. With multiple adhesive cover members 44 removed, a user may position the splinting member 38 over the IV site 90 and secure the securing members 28 and the portions of the main body 22 to skin of the patient.

The bottom portions of the pair of opposing securing members 28 may have an adhesive material 42 applied thereto. The bottom portion 26 of the main body 22 that does not carry the splinting member 38 may have an adhesive material 40 applied thereto. The main body 22, the securing members 28, and/or the splinting member 38 may comprise a flexible material whereby an IV site 90 may be covered by the IV splint cover 20 unless the main body 22, the securing members 28, and/or the splinting member 38 is/are expanded.

An overall width of the IV splint cover 20 may be about 50% or less than an overall length of the IV splint cover 20. A length of the main body 22 may be about 50% or less than the overall length of the IV splint cover 20. A width of the main body 22 may be substantially equal to the overall width of the IV splint cover 20. A length of each securing member 28 may be about 25% or less than the overall length of the IV splint cover 20. A width of each securing member 28 may be about 50% or less than the overall width of the IV splint cover 20. A length of the splinting member 38 may be less than a length of the main body 22. A width of the splinting member 38 may be less than a width of the main body 22. Those skilled in the art will appreciate that these dimensions may be increased or decreased as desired and the dimensions stated herein provided are exemplary. For example, and without limitation, the dimensions may be increased or decreased relative to the size of the IV site 90 or the body part.

Additional advantages are apparent with respect to the IV splint cover 20 according to the present invention. For example, use of the IV splint cover 20 results in a substantial decrease in costs associated with medical care. This is realized from costs saved in additional medical supplies associated with reinsertion of the IV, and also from a decrease in labor costs associated with the medical staff that would otherwise need to reinsert the IV. Reinsertion of the IV may also expose a patient to infection and additional and/or increased medical costs. There is also an inherent cost associated with patient comfort. Patients that do not require reinsertions of IV's are generally more comfortable, more satisfied, and can generally heal quicker, thereby decreasing inherent medical costs associated with prolonged recovery times. In addition, the IV splint cover 20 will make it more difficult to kink, shift or dislodge the IV line 80. As a result, there will be less chance for improper or delayed medication delivery or other fluids which a patient requires or as otherwise desired by medical staff to be provided to the patient to increase patient healing and decrease medical costs.

Figure 19:
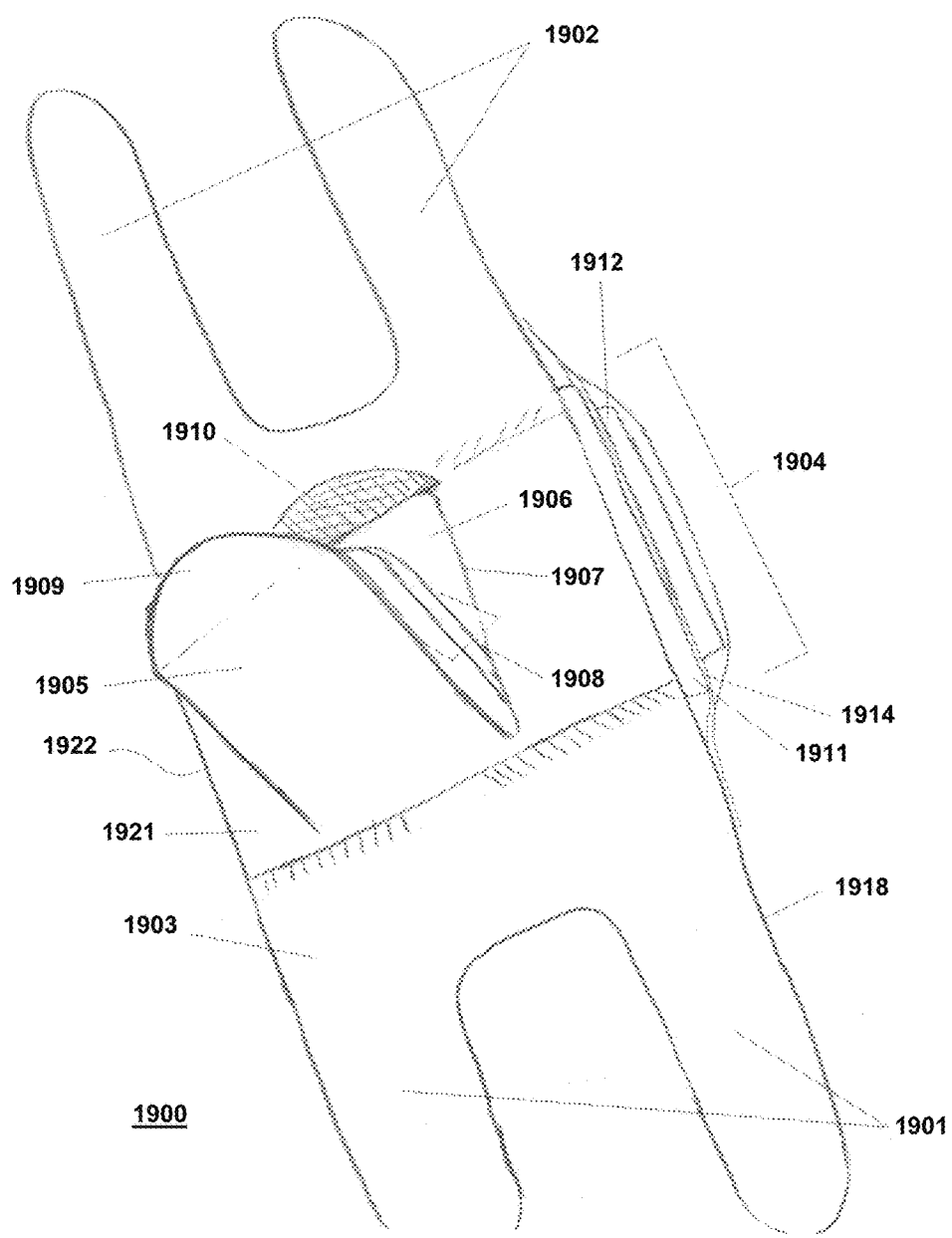
FIG. 19 is a top perspective view of an embodiment of the invention that includes a viewing door.

FIG. 19 illustrates a top perspective view of another embodiment of the invention. The invention, which has previously been referred to as an IV splint cover 20, may additionally be referred to as a cannulated tube protector 1900, an apparatus operable to facilitate the flow of fluids through a cannulated site, or an apparatus operable to protect and maintain positioning of a catheter. Like other embodiments, the cannulated tube protector 1900 may include a first pair of securing members 1901, a second pair of securing members 1902, a main body 1903, and a splinting member 1904. However, it is contemplated to be within the scope of this application that the pairs of securing members may be a single securing member on either side of the main body 1903. Likewise, there may be a plurality of securing members that may not be uniform pairs. Furthermore, it is contemplated to be within the scope herein that the securing members may be oriented in any configuration around the main body 1903 including angled. The splinting member may include a first elevated portion, defined as a platform 1911, and a second elevated portion 1912 positioned on the platform 1911. The combination of the platform 1911, which may be located adjacent the main body 1903, and the second elevated portion 1911 positioned on the platform 1911 may extend the splinting member 1904 distally from the main body 1903. The platform 1911 and the second elevated portion 1912 may be made of a foam type material. However, a person skilled in the art will recognize that they may be made of any material such as gauze, cotton, fabric, silicon or the like.

The cannulated tube protector 1900 may include sides, referred to as the apparatus edges 1918 that may include the longitudinal length of the cannulated tube protector 1900. A single apparatus edge 1918 may include the edge of a single securing member from the first pair of securing members 1901, the edge of the main body 1903, and a single securing member from the second pair of securing members 1902.

In one embodiment the apparatus edges 1918 may additionally include both edges of the platform 1911 and edges of the second elevated portion 1912. In this embodiment, the edges of the platform 1911 and the edges of the second elevated portion 1912 that face the apparatus edges 1918 may be flush with each other and flush with the apparatus edges 1918.

The platform 1911 and the second elevated portion 1912 may be rectangles whereby the longitudinal length of the rectangles run perpendicular to the longitudinal length of the cannulated tube protector 1900. The longitudinal length of the platform 1911 and the longitudinal length of the second elevated portion 1912 may be equal. However, it is contemplated to be within the scope of this application that the longitudinal length of the platform 1911 and the second elevated portion 1912 may not be equal.

By way of non-limiting example, the longitudinal length of the platform may be of greater length than the longitudinal length of the second elevated portion 1912. Furthermore, it is contemplated to be within the scope of this application that the platform 1911 and the second elevated portion 1912 may be any shape including square, circular, polygonal, or any combination thereof.

The latitudinal length of the platform 1911 and a latitudinal length of the second elevated portion 1912 may not be equal to each other. By way of non-limiting example, the latitudinal length of the platform 1911 may be of greater length than the latitudinal length of the second elevated portion 1912. The difference in latitudinal length may create a ledge 1914 between the platform 1911 and the second elevated portion 1912.

The cannulated tube protector 1900 may include a viewing door 1905. In some embodiments the viewing door 1905 may be medially located within the splinting member 1904. In other embodiments, the viewing door 1905 may be offset from a medial point of the viewing door 1905. The viewing door 1905 may be structured to open thereby exposing a viewing aperture, defined as a doorway 1906. The viewing door may be moveable between an open position to expose a viewing aperture and a closed position wherein the viewing aperture is not exposed. The doorway 1906 may include three perforated sections 1907 within the splinting member 1904. However, it is contemplated to be within the scope of this application that the doorway 1906 may include a single perforated section 1907 or a plurality of perforated sections 1907. Furthermore, the perforated section 1907 may be rounded, straight, or a combination of the two. The doorway 1906 may extend from a first surface 1921 of the main body 1903 to an opposing second surface 1922 of the main body 1903. Likewise, the viewing door thickness 1908 may be equal to the thickness of the splinting member 1904. This may include the thickness of both the platform 1911 and the second elevated portion 1912. In some embodiments the viewing door 1905 may be permanently affixed to the splinting member 1904 and in some embodiments the viewing door 1905 may be a removable portion of the cannulated tube protector 1900.

The viewing door 1905 may be a portion of the material removed from between either the first pair of securing members 1901 or the second pair of securing members 1902. The shape of the viewing door 1905 may correspond to the shape of the void between the securing members 1901, 1902. By way of non-limiting example, the void between the first pair of securing members 1901 may be outlined by opposing straight sides with curved corners. An adjacent side may run perpendicular to the straight sides and connect the curved corners. Correspondingly, the viewing door 1905, which created the void by its removal from this portion, may be a substantially rectangular shape with curved corners. The removed viewing door 1905 may then be attached to the main body 1903 via at least one of adhesion, hook-and-loop fastener, snap, button, silicon, and clip. However, one skilled in the art will appreciate that the viewing door 1905 may be any shape, including square, rectangular, triangular, circular, rounded, oval, and polygonal.

The viewing door 1905 may include a latch 1909 on the first surface 1921. The latch 1909 may be a thin membraned flap that extends distally from a main portion of the viewing door 1905. The latch 1909 may include a thickness of the first surface 1921 material, but not a thickness of the splinting member 1904. The viewing door 1905 may include a plurality of latches 1909 or a single latch 1909 assembly comprising a plurality of latch 1909 components. The latch 1909 may extend the entire length of the viewing door 1905, and in other embodiments it may be shorter or longer than a side of the viewing door 1905.

The latch 1909 may be removably secured to the cannulated tube protector 1900 at a latch attachment section 1910. The latch 1909 may be removably secured to the main body 1903 by at least one of adhesion, hook-and-loop fastener, snap, button, silicon, and clip. The latch 1909 may be semicircular in shape. However, the latch 1909 may be any shape including polygonal or rounded.

Figure 20:
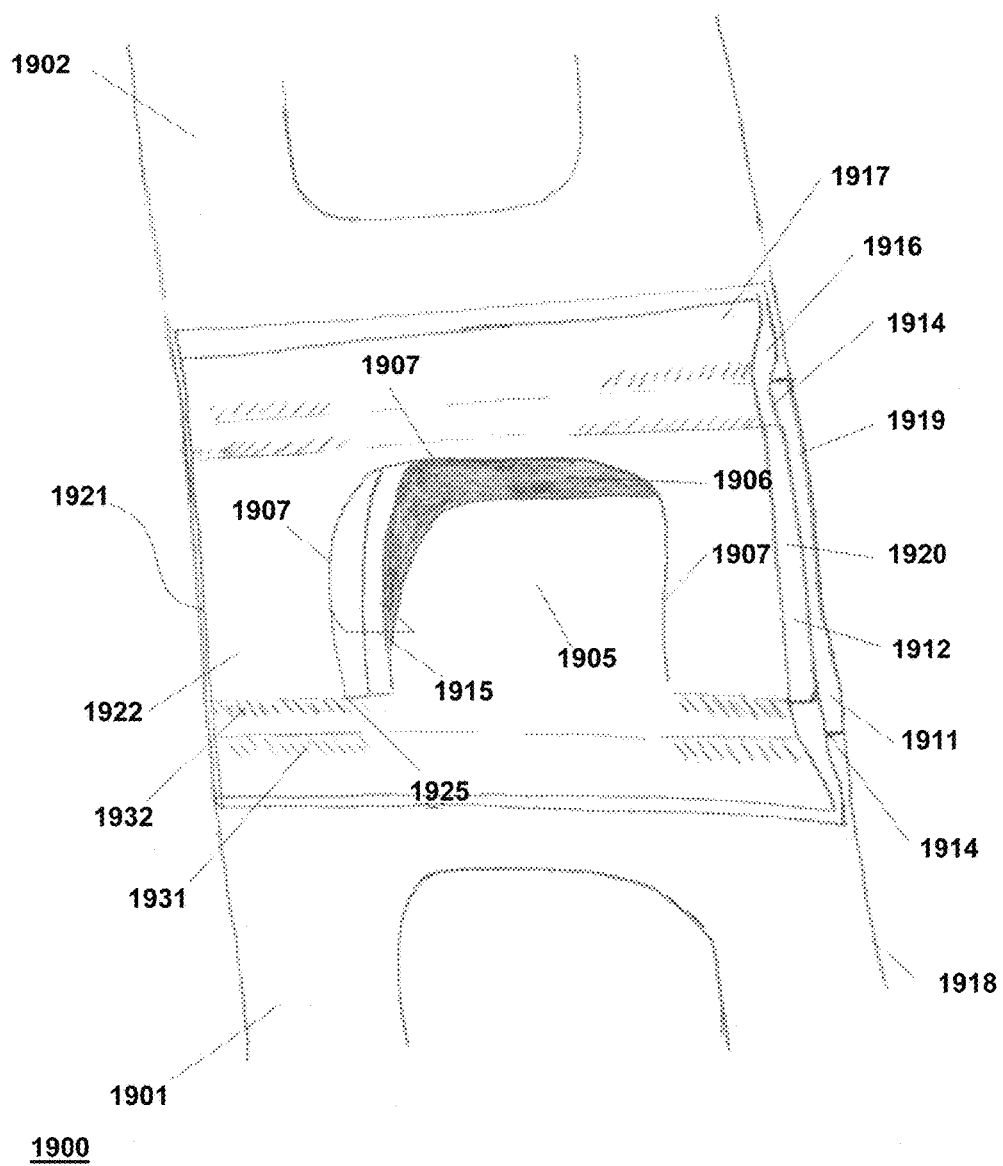
FIG. 20 is a bottom perspective view of the invention illustrated in FIG. 19.

FIG. 20 is a bottom perspective view of the cannulated tube protector 1900. As shown, the viewing door 1905 is pushed open from the second surface 1902 toward the first surface 1921 thereby exposing the splinting member thickness 1915 along perforated sections 1907 of the doorway 1906.

Also shown are a first cover pad 1916 and a second cover pad 1917. The first cover pad 1916 may be a flexible fabric type material that may adhere to the underside of the main body 1903 on one side, overlap the platform 1911, and adhere to the underside of the main body 1903 on an opposing side of the main body 1903. The first cover pad 1916 may secure the platform 1911 between the underside of the main body 1903 and the first cover pad 1916.

The second cover pad 1917 may be a flexible fabric type material that may adhere to the first cover pad 1916 on one side, overlap the second elevated portion 1912, and adhere to the first cover pad 1916 on an opposing side. The second cover pad 1917 may secure the second elevated portion 1912 between the first cover pad 1916 and the second cover pad 1917. Furthermore, the second cover pad 1917 may be made of the same material as the first cover pad 1916.

The second cover pad 1917 may extend past the first cover pad 1916 and adhere to the underside of the main body 1903. The second cover pad 1917 may cover the first cover pad 1916. Furthermore, the platform 1911, the first cover pad 1916, the second elevated portion 1912, and the second cover pad 1917 may be flush with, and include, a segment of the apparatus edges 1918.

The second cover pad 1917 may include an undulated surface. The undulated surface may include a first undulation 1931 between where the second cover pad 1917 is connected to the main body 1903 and/or the first cover pad 1916 and the ledge 1914. A second undulation 1932 may be between the ledge 1914 and a medial section where the second cover pad 1917 covers the second elevated portion 1912. This may form a latitudinal profile of the splinting member 1904 to include a bell curve frustum shape. A longitudinal profile of the splinting member 1904 may include a bell curve frustum shape. Additionally, both the latitudinal profile and longitudinal profile of the splinting member 1904 may include a bell curve frustum shape.

A first end of two of the perforated sections 1907 may abut the ledge 1914 proximate an edge of the second elevated portion 1912. The viewing door 1905 may utilize the ledge 1914 and the first and second undulations 1931, 1932 as a hinge to facilitate oscillation of the viewing door 1905. The slack afforded by the undulation at the ledge 1914 may allow for the viewing door 1905 to extend the first cover pad 1916 and the second cover pad 1917 from the second surface 1922 to open the viewing door 1905. The slack may also allow for the viewing door 1905 to fold along an undulation created by the platform 1911 on the first surface 1921 when the viewing door 1905 is opened.

Figure 21:
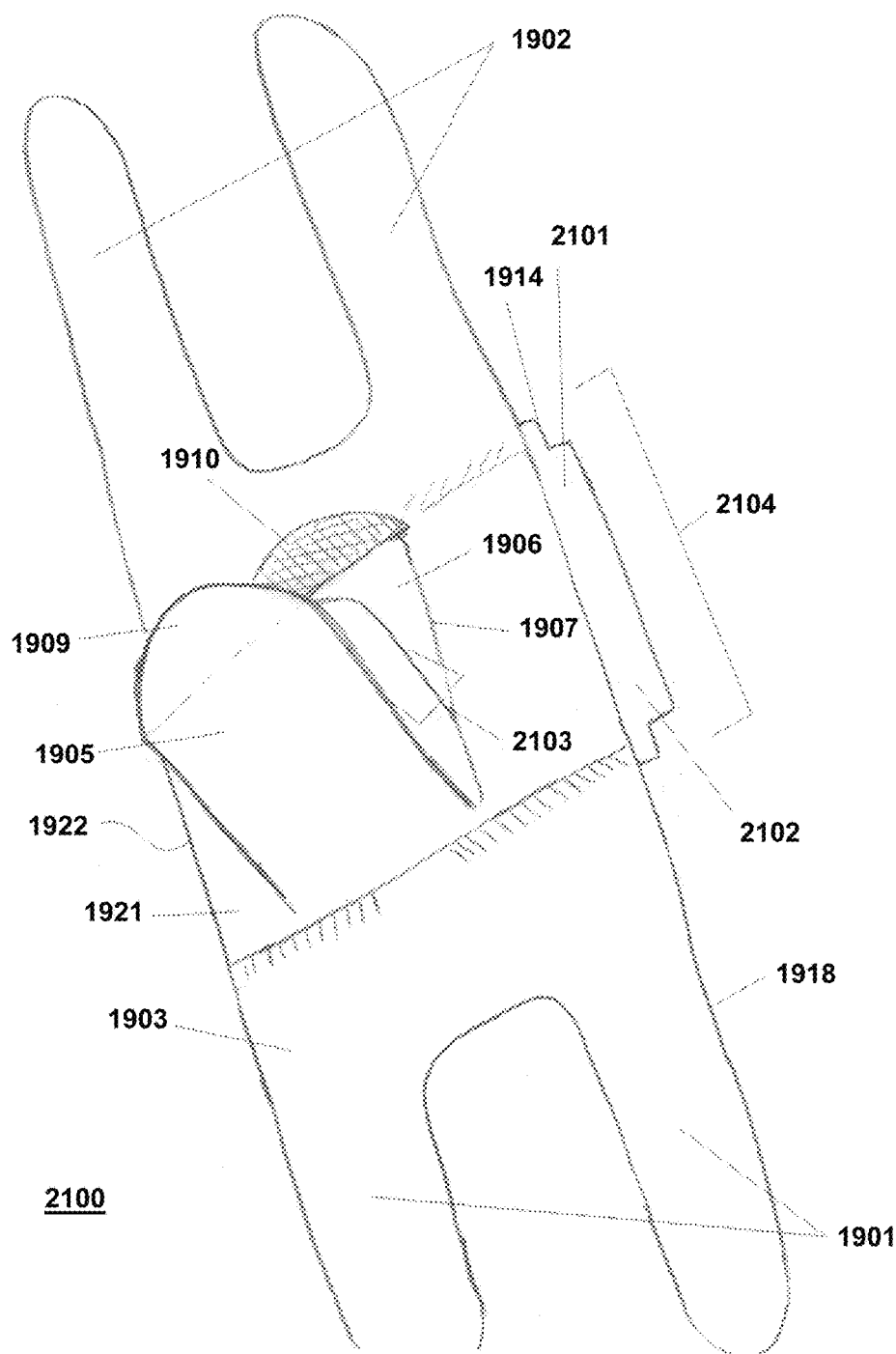
FIG. 21 is a top perspective view of another embodiment of the invention that includes a viewing door.

FIG. 21 illustrates another embodiment of the cannulated tube protector 2100 whereby the splinting member 2104 may be a single unit 2101. In this embodiment, the platform 1911 and the second elevated portion 1912 may combine to form the single unit 2101. In this embodiment the viewing door thickness 2103 and the splinting member thickness 2105 may still be equal. Therefore, the viewing door 1905 thickness may still equal the thickest part of the splinting member thickness 2105.

Figure 22:
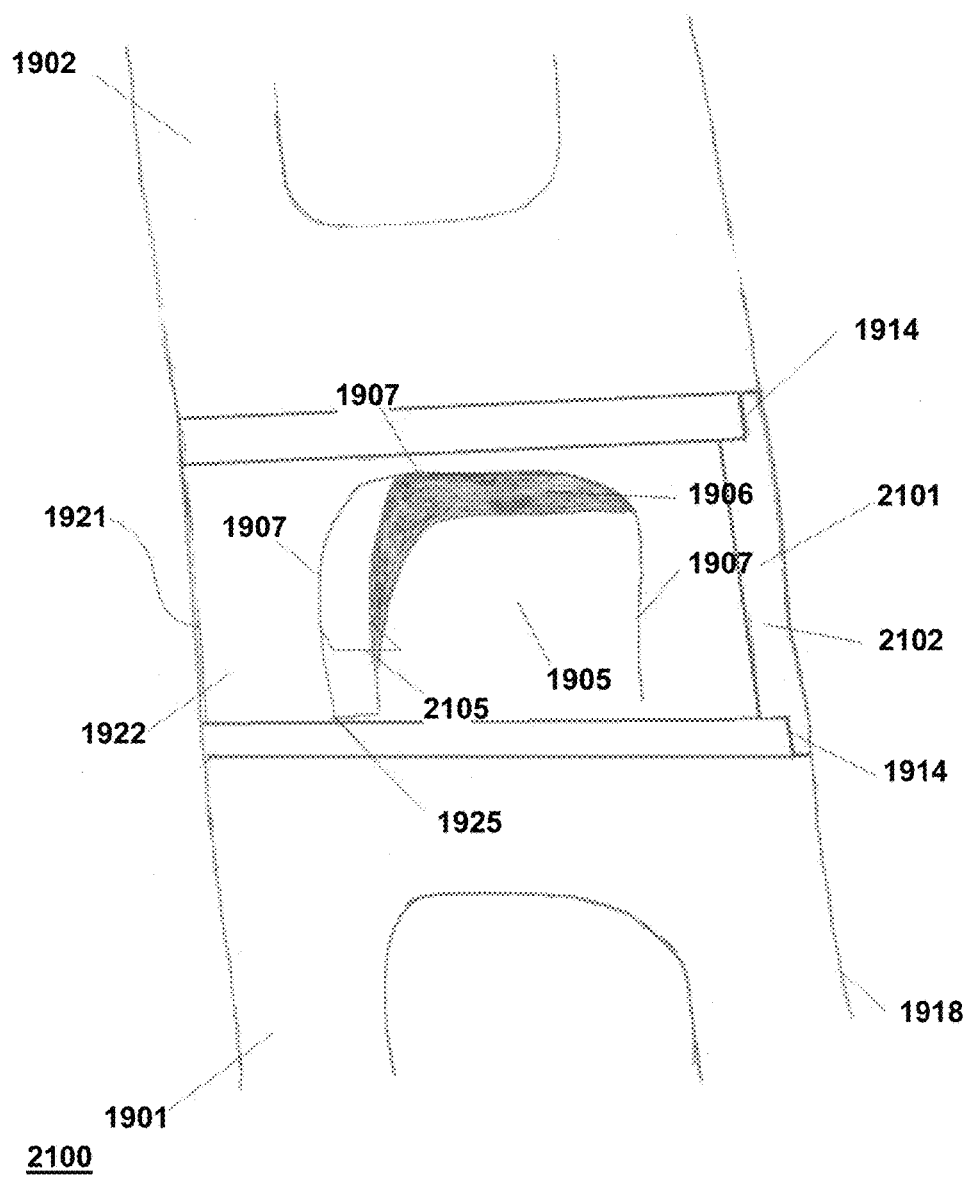
FIG. 22 is a bottom perspective view of the invention illustrated in FIG. 21.

FIG. 22 illustrates that the cannulated tube protector 2100 may include a splinting member 2104 solely made up of the single unit 2101. In other words, the splinting member 2104 may not include the first cover pad 1916 and the second cover pad 1917. However, the single unit 2101 may still include at least one side 2102 that is flush with and includes a segment of the apparatus edge 1918.

In any embodiment, the entire cannulated tube protector 1900, 2100 may be made of a translucent or transparent material such as silicon. However, in some embodiments only a portion of the cannulated tube protector 1900, 2100 may be made of translucent or transparent material. By way of non-limiting example, the viewing door 1905 may be made of translucent or transparent material, but the remaining portions of the cannulated tube protector 1900, 2100 may be opaque. Similarly, the viewing door 1905 may be opaque and the remaining portions of the cannulated tube protector 1900, 2100 may be translucent or transparent.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus, the scope of the invention should be determined by the appended claims and their legal equivalents, and not by the examples given.

The claims in the instant application are different than those of the parent application or other related applications. Applicant therefore rescinds any disclaimer of claim scope made in the parent application or any predecessor application in relation to the instant application. Any such previous disclaimer and the cited references that it was made to avoid, may need to be revisited. Further, any disclaimer made in the instant application should not be read into or against the parent application.

That which is claimed is:

1. A cannulated tube protector comprising:
   a main body;
   a splinting member carried on a bottom portion of the main body to be positioned against a cannulated tube and a patient's skin;
   a viewing door located within a portion of the main body and a corresponding portion of the splinting member;
   a first pair of securing members extending from the main body; and
   a second pair of securing members extending from the main body;
   wherein the viewing door is moveable between an open position to expose a viewing aperture and a closed position wherein the viewing aperture is not exposed.

2. The cannulated tube protector according to claim 1 wherein the splinting member extends from the main body to create an elevated splinting member portion.

3. The cannulated tube protector according to claim 2 wherein edge portions of the viewing door are initially connected to the main body by a perforated section.

4. The cannulated tube protector according to claim 2 wherein the viewing door has a thickness equal to a combined thickness of the main body and the elevated splinting member.

5. The cannulated tube protector according to claim 1 wherein the viewing door comprises at least one latch extending from an edge portion of the viewing door and configured to facilitate opening the viewing door.

6. The cannulated tube protector according to claim 5 wherein the at least one latch is configured to removably secure to the main body by at least one of adhesion, hook-and-loop fastener, snap, button, silicon, and clip.

7. The cannulated tube protector according to claim 1 wherein the splinting member comprises a first elevated portion, defined as a platform, and a second elevated portion positioned on the platform.

8. The cannulated tube protector according to claim 7 wherein the platform has at least one of a length and width greater than the second elevated portion creating at least one ledge between the platform and the second elevated portion.

9. The cannulated tube protector according to claim 7 wherein the platform and the second elevated portion are a single unit.

10. An apparatus operable to facilitate the flow of fluids through a cannulated site comprising:
    a main body;
    a first pair of securing members extending from the main body;
    a second pair of securing members extending from the main body;
    a splinting member carried on a bottom portion of the main body; and
    a rotatable viewing door positioned within the main body and the splinting member.

11. The apparatus according to claim 10 wherein the splinting member comprises one of a longitudinal and latitudinal profile with a bell curved frustum shape.

12. The apparatus according to claim 10 wherein at least one of the main body, the first pair of securing members, the second pair of securing members, and the splinting member comprise a flexible material configured to be lifted to view an active intravenous site.

13. The apparatus according to claim 10 wherein the viewing door is configured to be opened to view an active cannulated site.

14. The apparatus according to claim 10 wherein the viewing door is at least one of square, rectangular, triangular, circular, rounded, oval, polygonal, and a combination thereof.

15. The apparatus according to claim 10 wherein the viewing door is configured as a removeable segment taken from between the first pair of securing members; and wherein the viewing door is configured to be removably secured to the main body via one of adhesion, hook-and-loop fastener, snap, button, silicon, and clip.

16. The apparatus according to claim 15 wherein the splinting member comprises a first elevated portion, defined as a platform, and a second elevated portion positioned on the platform; and wherein the platform has a longitudinal length that is greater than a longitudinal length of the second elevated portion; and wherein the latitudinal length of the platform is equal to the latitudinal length of the second elevated portion.

17. The apparatus according to claim 15 wherein the splinting member comprises a first elevated portion, defined as a platform, and a second elevated portion positioned on the platform; and wherein the platform has a latitudinal length that is greater than a latitudinal length of the second elevated portion; and wherein the longitudinal length of the platform is equal to the longitudinal length of the second elevated portion.

18. The apparatus of claim 17 wherein the splinting member comprises a first elevated portion, defined as a platform, and a second elevated portion positioned on the platform; and wherein the platform has a latitudinal length that is greater than a latitudinal length of the second elevated portion; and wherein the longitudinal length of the platform is equal to the longitudinal length of the second elevated portion.

19. The apparatus of claim 17 wherein the splinting member comprises a first elevated portion, defined as a platform, and a second elevated portion positioned on the platform; and wherein the platform has a latitudinal length that is greater than a latitudinal length of the second elevated portion; and wherein the longitudinal length of the platform is equal to the longitudinal length of the second elevated portion.

20. An apparatus operable to protect and maintain positioning of a catheter comprising:
    a main body;
    a first securing member extending from the main body;
    a second securing member extending from the main body; and
    a splinting member carried on a bottom portion of the main body;
    a viewing door positioned within the main body and the splinting member;
    wherein the viewing door is configured to open thereby exposing a viewing aperture, defined as a doorway;

wherein the doorway extends from a first surface of the main body through to an opposing surface of the splinting member; and wherein the viewing door comprises at least one latch configured to facilitate opening the viewing door.

* * * * *